US012667415B2

(12) United States Patent
Keyes et al.

(10) Patent No.: US 12,667,415 B2
(45) Date of Patent: *Jun. 30, 2026

(54) BASKET CATHETER WITH CLOVERLEAF STRUCTURE TO PROVIDE PREDETERMINED LATERAL STIFFNESS AND AXIAL STRAIN

(71) Applicant: Biosense Webster (Israel) Ltd., Yokneam (IL)

(72) Inventors: Joseph Thomas Keyes, Sierra Madre, CA (US); Kevin Justin Herrera, West Covina, CA (US); Christopher Thomas Beeckler, Brea, CA (US); Athanassios Papaioannou, Irvine, CA (US); Justin George Lichter, Irvine, CA (US); Kevin Mark Okarski, Monrovia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 366 days.

This patent is subject to a terminal disclaimer.

(21) Appl. No.: 18/192,411

(22) Filed: Mar. 29, 2023

(65) Prior Publication Data

US 2023/0346466 A1    Nov. 2, 2023

Related U.S. Application Data

(60) Provisional application No. 63/477,819, filed on Dec. 29, 2022, provisional application No. 63/477,404, (Continued)

(51) Int. Cl.
| | |
|---|---|
| *A61B 5/00* | (2006.01) |
| *A61B 18/14* | (2006.01) |
| *A61B 18/00* | (2006.01) |

(52) U.S. Cl.
CPC ..................... *A61B 18/1492* (2013.01); *A61B 2018/0016* (2013.01); *A61B 2018/00267* (2013.01);
(Continued)

(58) Field of Classification Search
CPC ........ A61B 18/1492; A61B 2018/0016; A61B 2018/00267; A61B 2018/00357;
(Continued)

(56) References Cited

U.S. PATENT DOCUMENTS

| | | | |
|---|---|---|---|
| 3,952,747 A | 4/1976 | Kimmell, Jr. | |
| 4,699,147 A | 10/1987 | Chilson et al. | |

(Continued)

FOREIGN PATENT DOCUMENTS

| | | |
|---|---|---|
| CN | 105761835 A | 7/2016 |
| CN | 107440790 A | 12/2017 |

(Continued)

OTHER PUBLICATIONS

Extended European Search Report & Opinion dated Sep. 19, 2023, from corresponding European Application No. 23170233.3.
(Continued)

*Primary Examiner* — Ronald Hupczey, Jr.
*Assistant Examiner* — Ana Veruska Guerrero

(57) ABSTRACT

A medical probe is presented including an expandable basket assembly coupled to a distal end of a tubular shaft. The basket assembly includes a cloverleaf cutout structure at its distal end and spines extending proximally from the cloverleaf structure and coupling to the tubular shaft. The cloverleaf structure includes a sinusoidal-like member extending from one spine to an adjacent spine in a direction around the longitudinal axis. Dimensions of the sinusoidal-like member can be configured to provide a lateral stiffness of the expandable basket assembly within a predetermined range and a maximum peak stress during retraction of the
(Continued)

expandable basket assembly into an intermediate catheter such that the maximum peak stress is less than a predetermined threshold.

20 Claims, 23 Drawing Sheets

Related U.S. Application Data filed on Dec. 28, 2022, provisional application No. 63/336,094, filed on Apr. 28, 2022, provisional application No. 63/336,023, filed on Apr. 28, 2022.

(52) U.S. Cl.
 CPC ............... *A61B 2018/00357* (2013.01); *A61B 2018/00577* (2013.01); *A61B 2018/00613* (2013.01); *A61B 2018/00767* (2013.01); *A61B 2018/1405* (2013.01); *A61B 2018/1467* (2013.01)

(58) Field of Classification Search
 CPC ........... A61B 2018/00577; A61B 2018/00613; A61B 2018/00767; A61B 2018/1405; A61B 2018/1467; A61B 5/062; A61B 5/063; A61B 5/068; A61B 5/4848; A61B 5/287; A61B 5/333; A61B 5/367; A61B 5/6858; A61B 5/6859; A61B 2018/00375; A61B 2218/002
 See application file for complete search history.

(56) References Cited

U.S. PATENT DOCUMENTS

| | | | |
|---|---|---|---|
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |
| 5,324,284 | A | 6/1994 | Imran |
| 5,345,936 | A | 9/1994 | Pomeranz et al. |
| 5,365,926 | A | 11/1994 | Desai |
| 5,391,199 | A | 2/1995 | Ben-Haim |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,443,489 | A | 8/1995 | Ben-Haim |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,558,091 | A | 9/1996 | Acker et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,718,241 | A | 2/1998 | Ben-Haim et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,239 | A | 7/1998 | Webster, Jr. |
| 5,782,899 | A | 7/1998 | Imran |
| 5,823,189 | A | 10/1998 | Kordis |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,944,022 | A | 8/1999 | Nardella et al. |
| 5,968,040 | A | 10/1999 | Swanson et al. |
| 5,983,126 | A | 11/1999 | Wittkampf |
| 6,014,579 | A | 1/2000 | Pomeranz et al. |
| 6,014,590 | A | 1/2000 | Whayne et al. |
| 6,023,638 | A | 2/2000 | Swanson |
| 6,119,030 | A | 9/2000 | Morency |
| 6,142,993 | A | 11/2000 | Whayne et al. |
| 6,172,499 | B1 | 1/2001 | Ashe |
| 6,198,974 | B1 | 3/2001 | Webster, Jr. |
| 6,216,043 | B1 | 4/2001 | Swanson et al. |
| 6,216,044 | B1 | 4/2001 | Kordis |
| 6,239,724 | B1 | 5/2001 | Doron et al. |
| 6,332,089 | B1 | 12/2001 | Acker et al. |
| 6,428,537 | B1 | 8/2002 | Swanson et al. |
| 6,456,864 | B1 | 9/2002 | Swanson et al. |
| 6,484,118 | B1 | 11/2002 | Govari |
| 6,574,492 | B1 | 6/2003 | Ben-Haim et al. |
| 6,584,345 | B2 | 6/2003 | Govari |
| 6,600,948 | B2 | 7/2003 | Ben-Haim et al. |
| 6,618,612 | B1 | 9/2003 | Acker et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,788,967 | B2 | 9/2004 | Ben-Haim et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 6,987,995 | B2 | 1/2006 | Drysen |
| 7,048,734 | B1 | 5/2006 | Fleischman et al. |
| 7,142,903 | B2 | 11/2006 | Rodriguez et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,274,957 | B2 | 9/2007 | Drysen |
| 7,377,906 | B2 | 5/2008 | Selkee |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| 7,536,218 | B2 | 5/2009 | Govari et al. |
| 7,591,799 | B2 | 9/2009 | Selkee |
| 7,593,760 | B2 | 9/2009 | Rodriguez et al. |
| RE41,334 | E | 5/2010 | Beatty et al. |
| 7,720,517 | B2 | 5/2010 | Drysen |
| 7,756,576 | B2 | 7/2010 | Levin |
| 7,794,473 | B2 | 9/2010 | Tessmer et al. |
| 7,846,157 | B2 | 12/2010 | Kozel |
| 7,848,787 | B2 | 12/2010 | Osadchy |
| 7,853,302 | B2 | 12/2010 | Rodriguez et al. |
| 7,869,865 | B2 | 1/2011 | Govari et al. |
| 7,930,018 | B2 | 4/2011 | Harlev et al. |
| 8,000,765 | B2 | 8/2011 | Rodriguez et al. |
| 8,007,495 | B2 | 8/2011 | McDaniel et al. |
| 8,021,327 | B2 | 9/2011 | Selkee |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,275,440 | B2 | 9/2012 | Rodriguez et al. |
| 8,295,902 | B2 | 10/2012 | Salahieh et al. |
| 8,346,339 | B2 | 1/2013 | Kordis et al. |
| 8,357,152 | B2 | 1/2013 | Govari et al. |
| 8,435,232 | B2 | 5/2013 | Aeby et al. |
| 8,447,377 | B2 | 5/2013 | Harlev et al. |
| 8,456,182 | B2 | 6/2013 | Bar-Tal et al. |
| 8,475,450 | B2 | 7/2013 | Govari et al. |
| 8,498,686 | B2 | 7/2013 | Grunewald |
| 8,517,999 | B2 | 8/2013 | Pappone et al. |

(56) References Cited

U.S. PATENT DOCUMENTS

| | | |
|---|---|---|
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,728,065 B2 | 5/2014 | Fish et al. |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,848,795 B2 | 12/2017 | Marecki et al. |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,342,608 B2 | 7/2019 | Wang et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,467 B2 | 4/2020 | Viswanathan et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,688,278 B2 | 6/2020 | Beeckler et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,932,685 B2 | 3/2021 | Wu |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,071,585 B2 | 7/2021 | Zhang et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0198522 A1 | 12/2002 | Kordis et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0058813 A1 | 3/2006 | Teague et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2009/0149848 A1 | 6/2009 | Werneth et al. |
| 2010/0063478 A1 | 3/2010 | Selkee |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0271136 A1 | 10/2012 | Kordis et al. |
| 2012/0271138 A1 | 10/2012 | Kordis et al. |
| 2012/0271140 A1 | 10/2012 | Kordis et al. |
| 2013/0090651 A1 | 4/2013 | Smith |
| 2013/0150693 A1 | 6/2013 | D'Angelo |
| 2013/0172715 A1 | 7/2013 | Just et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0088588 A1 | 3/2014 | Jarrard |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |

(56)  References Cited

U.S. PATENT DOCUMENTS

| | | |
|---|---|---|
| 2014/0276746 A1 | 9/2014 | Nabutovsky et al. |
| 2014/0288552 A1 | 9/2014 | Kunis |
| 2014/0309512 A1 | 10/2014 | Govari et al. |
| 2014/0309513 A1 | 10/2014 | Fish et al. |
| 2014/0350551 A1 | 11/2014 | Raatikka et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0223757 A1 | 8/2015 | Werneth et al. |
| 2015/0250424 A1 | 9/2015 | Govari et al. |
| 2015/0270634 A1 | 9/2015 | Buesseler et al. |
| 2015/0282859 A1 | 10/2015 | Bencini et al. |
| 2015/0342491 A1 | 12/2015 | Marecki et al. |
| 2015/0342532 A1 | 12/2015 | Basu et al. |
| 2015/0351625 A1 | 12/2015 | Schroth et al. |
| 2015/0366508 A1 | 12/2015 | Chou et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0324573 A1 | 11/2016 | Mickelson et al. |
| 2016/0338770 A1 | 11/2016 | Bar-Tal et al. |
| 2017/0027638 A1 | 2/2017 | Solis |
| 2017/0035496 A1 | 2/2017 | Nagale et al. |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0164858 A1 | 6/2017 | Basu |
| 2017/0172442 A1 | 6/2017 | Govari |
| 2017/0172651 A1 | 6/2017 | Gross et al. |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319140 A1* | 11/2017 | Wu ..................... A61B 5/6859 |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0000540 A1 | 1/2018 | Ogle et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0116595 A1 | 5/2018 | Ruppersberg |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0192959 A1 | 7/2018 | Mou et al. |
| 2018/0206792 A1 | 7/2018 | Auerbach et al. |
| 2018/0228439 A1 | 8/2018 | Wu et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0303546 A1 | 10/2018 | Buysman et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125338 A1* | 5/2019 | Shelton, IV ........... A61B 17/00 |
| 2019/0125437 A1 | 5/2019 | Govari et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0336210 A1 | 11/2019 | Beeckler et al. |
| 2019/0343580 A1 | 11/2019 | Nguyen et al. |
| 2019/0350567 A1 | 11/2019 | Cummins et al. |
| 2019/0350647 A1 | 11/2019 | Ramberg et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015876 A1 | 1/2020 | Chou et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0197082 A1 | 6/2020 | Daniel et al. |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |

(56)                    References Cited

U.S. PATENT DOCUMENTS

| 2020/0305946 A1 | 10/2020 | Desimone et al. |
| 2020/0375657 A1 | 12/2020 | Olson et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077180 A1 | 3/2021 | Govari et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093376 A1 | 4/2021 | Harlev et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161582 A1 | 6/2021 | Byrd et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0187254 A1 | 6/2021 | Beeckler et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0236815 A1 | 8/2021 | Waldstreicher et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2021/0369339 A1 | 12/2021 | Salazar et al. |
| 2022/0071695 A1 | 3/2022 | Beeckler et al. |
| 2022/0071696 A1 | 3/2022 | Govari et al. |
| 2022/0110679 A1 | 4/2022 | Wang et al. |
| 2022/0304745 A1 | 9/2022 | Olson |
| 2022/0378498 A1 | 12/2022 | Zhang et al. |
| 2022/0387051 A1 | 12/2022 | Girdhar et al. |
| 2023/0000550 A1 | 1/2023 | Nedved et al. |
| 2023/0130692 A1 | 4/2023 | Wang et al. |
| 2023/0225790 A1* | 7/2023 | Okarski ............. A61B 18/1492 606/41 |
| 2023/0346455 A1* | 11/2023 | Beeckler ................ A61B 5/287 |
| 2023/0346459 A1* | 11/2023 | Beeckler ............ A61B 18/1492 |
| 2023/0346462 A1* | 11/2023 | Beeckler ............ A61B 18/1492 |
| 2023/0346464 A1* | 11/2023 | Beeckler ............ A61B 18/1492 |
| 2024/0216045 A1* | 7/2024 | Keyes ................ A61B 18/1492 |
| 2025/0057589 A1 | 2/2025 | Sandquist et al. |
| 2025/0185969 A1 | 6/2025 | Selkee et al. |

FOREIGN PATENT DOCUMENTS

| CN | 111225627 A | 6/2020 | |
| CN | 111248993 A | 6/2020 | |
| CN | 111248996 A | 6/2020 | |
| CN | 112399824 A | 2/2021 | |
| CN | 213665310 U | 7/2021 | |
| CN | 113995501 A | 2/2022 | |
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2201905 A1 * | 6/2010 | ......... A61B 18/1492 |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 2578173 B1 | 6/2017 | |
| EP | 3181082 A1 | 6/2017 | |
| EP | 3238645 A1 | 11/2017 | |
| EP | 2884931 B1 | 1/2018 | |
| EP | 3315086 A1 | 5/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3791816 A2 * | 3/2021 | ............. A61B 34/20 |
| EP | 3972510 A1 | 3/2022 | |
| EP | 4115834 A1 | 1/2023 | |
| WO | WO-9421167 A1 | 9/1994 | |
| WO | WO-9421169 A1 | 9/1994 | |
| WO | WO-9625095 A1 | 8/1996 | |
| WO | WO-9634560 A1 | 11/1996 | |
| WO | WO-0182814 A2 | 5/2002 | |
| WO | WO-2004087249 A2 | 10/2004 | |
| WO | WO-2012100185 A2 | 7/2012 | |
| WO | WO-2013052852 A1 | 4/2013 | |
| WO | WO-2013162884 A1 | 10/2013 | |
| WO | WO-2013173917 A1 | 11/2013 | |
| WO | WO-2013176881 A1 | 11/2013 | |
| WO | WO-2014176205 A1 | 10/2014 | |
| WO | WO-2016019760 A1 | 2/2016 | |
| WO | WO-2016044687 A1 | 3/2016 | |
| WO | WO-2018111600 A1 | 6/2018 | |
| WO | WO-2018191149 A1 | 10/2018 | |
| WO | WO-2019084442 A1 | 5/2019 | |
| WO | WO-2019143960 A1 | 7/2019 | |
| WO | 2019156942 A1 | 8/2019 | |
| WO | WO-2020026217 A1 | 2/2020 | |
| WO | 2020194216 A1 | 10/2020 | |
| WO | WO-2020206328 A1 | 10/2020 | |
| WO | 2021126980 A1 | 6/2021 | |
| WO | 2022001908 A1 | 1/2022 | |

OTHER PUBLICATIONS

Extended European Search Report dated Feb. 2, 2023, from Corresponding European Application No. 22194819.3, 8 pages.
Extended European Search Report and Opinion dated Jun. 1, 2023, from corresponding European Application No. 23152493.5.
Extended European Search Report and Opinion dated Jun. 7, 2023, from corresponding European Application No. 23152399.4.
Extended European Search Report and Opinion dated Jun. 12, 2023, from corresponding European Application No. 23152448.9.
Extended European Search Report dated Jun. 13, 2023, from Corresponding European Application No. 23152458.8, 12 pages.
Extended European Search Report and Opinion dated Sep. 6, 2023, from corresponding European Application No. 23152472.9.
Extended European Search Report & Search Opinion dated Sep. 19, 2023, from corresponding European Application No. 23170325.7.
Extended European Search Report & Search Opinion dated Sep. 21, 2023, from corresponding European Application No. 23170230.9.
Extended European Search Report & Search Opinion dated Sep. 21, 2023, from corresponding European Application No. 23170409.9.

(56)                    References Cited

OTHER PUBLICATIONS

Extended European Search Report & Search Opinion dated Jan. 2,
2024, from corresponding European Application No. 23170297.8.
First Search dated Jun. 9, 2023, from corresponding Chinese
Application No. 202310477352.5.

* cited by examiner

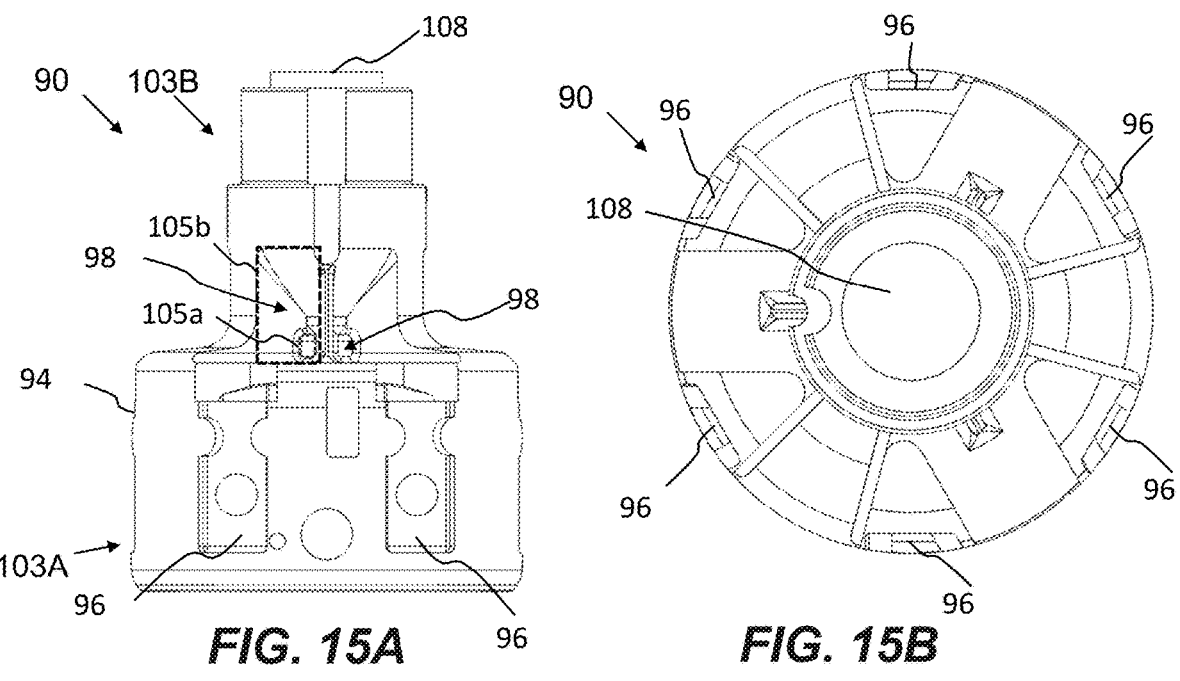
FIG. 15A
FIG. 15B
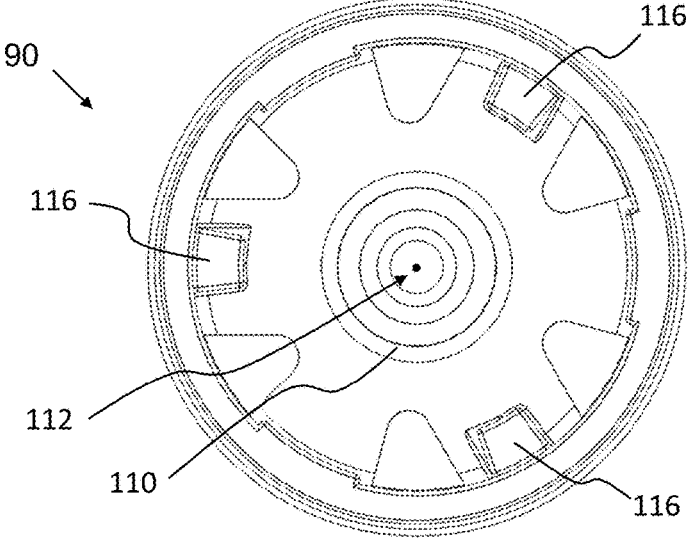
FIG. 15C

BASKET CATHETER WITH CLOVERLEAF STRUCTURE TO PROVIDE PREDETERMINED LATERAL STIFFNESS AND AXIAL STRAIN

CROSS-REFERENCE TO RELATED APPLICATIONS

This application claims priority under 35 U.S.C. § 119 to prior filed U.S. Provisional Patent Application No. 63/336, 023 filed Apr. 28, 2022, U.S. Provisional Patent Application No. 63/336,094 filed Apr. 28, 2022, U.S. Provisional Patent Application No. 63/477,404 filed Dec. 28, 2022, and U.S. Provisional Patent Application No. 63/477,819 filed Dec. 29, 2022 each of which are hereby incorporated by reference as if set forth in full herein.

FIELD

The present invention relates generally to medical devices, and in particular catheters with substantially ovoid or trapezoidal electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that can reduce some thermal risks associated with RF ablation but may present tissue damage due to the very low temperature nature of such devices. Maneuvering cryoablation devices and selectively applying cryoablation, however, is generally more challenging compared to RF ablation; therefore, cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the Appendix of priority Provisional Patent Application U.S. 63/477,404.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly, alternative catheter geometries, and alternative electrode shapes and sizes in general.

SUMMARY

A medical probe is presented including an expandable basket assembly coupled to a distal end of a tubular shaft. The basket assembly includes a cloverleaf cutout structure at its distal end and spines extending proximally from the cloverleaf structure and coupling to the tubular shaft. The cloverleaf structure includes a sinusoidal-like member extending from one spine to an adjacent spine in a direction around the longitudinal axis. Dimensions of the sinusoidal-like member can be configured to provide a lateral stiffness of the expandable basket assembly within a predetermined range and a maximum peak stress during retraction of the expandable basket assembly into an intermediate catheter such that the maximum peak stress is less than a predetermined threshold.

An example medical probe can include a tubular shaft and an expandable basket assembly. The tubular shaft can have a proximal end and a distal end and can extend along a longitudinal axis of the medical probe. The expandable basket assembly can be coupled to the distal end of the tubular shaft. The basket assembly can include a plurality spines extending along the longitudinal axis from a proximal central proximal spine portion to a distal spine portion. The distal spine portion can define a cloverleaf structure. The cloverleaf structure can be disposed radially around the longitudinal axis. The cloverleaf structure can define a central cutout with a central area disposed about the longitudinal axis. The cloverleaf structure can include a sinusoidal-like member extending from one spine to an adjacent spine in a direction around the longitudinal axis. The sinusoidal-like member can meander around a first virtual circle, a second virtual circle, and a third virtual circle. The first virtual circle has a first radius. The first virtual circle can have its center located at a first distance to the longitudinal axis. The second virtual circle has a second radius. The second virtual circle can have its center located at a second distance smaller than the first distance to the longitudinal axis. The third virtual circle has a third radius approximately equal to the first radius. The third virtual circle can have its center located at a third distance approximately equal to the first distance to the longitudinal axis. The cloverleaf structure can define a height measured from a point on a perimeter of the second virtual circle to a neck directly away from the longitudinal axis in relation to the second virtual circle and between an adjacent first virtual circle and second virtual circle. The first radius, second radius, third radius, and height can be configured to provide a lateral stiffness of the expandable basket assembly within a predetermined range.

The first radius, second radius, third radius, and height being configured to provide a maximum peak stress during retraction of the expandable basket assembly into an intermediate catheter such that the maximum peak stress is less than a predetermined threshold.

The first radius can measure about 33% of the height. The second radius can measure about 39% of the height. The third radius can measure about 33% of the height. A minimum width of the sinusoidal-like member can measure about 25% of the height.

The first radius can measure between 31% and 35% of the height. The second radius can measure between 37% and 41% of the height. The third radius can measure between 31% and 35% of the height. The minimum width of the sinusoidal-like member can measure between 23% and 27% of the height.

The central area can have an approximately 0.8 mm-squared area. A fourth virtual circle encircling the sinusoidal-like member can have an area approximately 14 times greater than the central area. Each of the first and third virtual circles can be located at a first distance from the central axis while the second virtual circle is located at a second distance of approximately ½ that of the first distance.

The sinusoidal-like member can be tangential to the central circle.

The expandable basket assembly can include a coating covering the sinusoidal-like member and a central cutout circumscribed by the sinusoidal-like member.

The expandable basket assembly can include a coating covering a majority of the sinusoidal-like member and comprises an opening at the longitudinal axis.

A cross-sectional shape of each electrode can have a substantially ovoid or trapezoidal shape.

Each of the spines can include at least one retention member extending generally transverse to the spine.

The medical probe can further include a plurality of electrodes. Each electrode of the plurality of electrodes can have a body defining a hollow portion extending through the body of the electrode so that a spine can be inserted into the hollow portion and retained by the at least one retention member.

The at least one retention member can include a bow shaped member. The at least one retention member can include two bow shaped members disposed in opposite direction and transverse to a longer length of each spine.

The at least one retention member can include first and second sets of retention members spaced apart along the spines. The first set can include two bow shaped members disposed in opposite direction and transverse to a longer length of each spine. The second set can include two bow shaped members disposed in opposite direction and transverse to a longer length of each spine so that each electrode is captured between the first and second sets of retention members.

The plurality of spines can extend from the proximal central spine portion in an equiangular pattern such that respective angles between respectively adjacent spines are approximately equal.

The medical probe can further include a plurality of electrically insulative jackets each disposed between a respective spine of the plurality of spines and a respective electrode, thereby electrically isolating the respective electrode from the respective spine.

The sinusoidal-like member can have an inner arc around the second virtual circle such that the inner arc is entirely positioned less than the second distance from the longitudinal axis. The sinusoidal-like member can have an outer portion around the first virtual circle and around the second virtual circle such that the outer portion is entirely positioned greater than the second distance from the longitudinal axis. A majority of the outer portion of the sinusoidal-like member can be covered by a respective jacket of the electrically insulative jackets.

At least a portion of the inner arc of the sinusoidal-like member can be exposed to environment.

A distal portion of each of the plurality of electrically insulative jackets can taper outward and inward, following a curvature of the outer portion of the sinusoidal-like member. The distal portion of each of the plurality of electrically insulative jackets can abut the distal portion of an adjacent insulative jacket.

The medical probe can further include two electrodes coupled to a respective spine for each spine of the plurality of spines.

The medical probe can further include a wire disposed inside a respective jacket the plurality of electrically insulative jackets, wherein the wire is electrically connected to the respective electrode.

The plurality of spines can include a material selected from a group consisting of nitinol, cobalt chromium, stainless steel, titanium, and combinations hereof.

Each electrode can include of a material selected from stainless steel, cobalt chromium, gold, platinum, palladium, and alloys or combinations hereof.

The medical probe can further include a plurality of electrodes configured to deliver electrical pulses for irreversible electroporation, the pulses including a peak voltage of at least 900 volts (V).

The plurality of spines can be configured to form an approximately spherically-shaped basket assembly when in the expanded form.

The plurality of spines can be configured form an approximately oblate-spheroid basket assembly when in the expanded form.

The medical probe can further include irrigation ports disposed in the proximal portion of the basket to deliver an irrigation fluid to the plurality of electrodes.

The central cutout can approximate a central circle with a central area and wherein the cloverleaf structure is disposed within a fourth circle with its center on the longitudinal axis so that portions of the cloverleaf close to the center circle is spaced apart along the longitudinal axis with respect to portions of the cloverleaf close to the fourth circle thereby defining a concave cloverleaf structure.

The cloverleaf structure can be concave with its center extending towards the proximal central spine portion of the basket to approximate a concave surface disposed about the longitudinal axis.

A reference electrode can be disposed proximate the distal end of the tubular shaft.

A spine retention hub can be coupled to the distal end of the tubular shaft to connect the spines to the retention hub.

A cylindrical projection can be provided to locate the reference electrode on the projection.

The spine retention hub can include outlet ports to allow fluid delivered to the distal end tubular shaft to exit the outlet ports into a volume surrounded by the basket spines.

An example method can include the following steps executed in a variety of orders and with interleaving steps as understood by a person skilled in the pertinent art. The method can include cutting a tubular frame including a plurality of spines extending along the longitudinal axis from a proximal spine portion to a distal spine portion, the distal spine portion defining a cloverleaf structure disposed radially around the longitudinal axis, the tubular frame being configured to move from a tubular shape to an expanded basket shape. In the expanded basket shape, the plurality of spines bow away from the longitudinal axis, the cloverleaf structure defines a central cutout with a central area disposed about the longitudinal axis, and the cloverleaf structure comprises a sinusoidal-like member extending from one spine to an adjacent spine in a direction around the longitudinal axis. In the expanded basket shape, the sinusoidal-like member meanders around a first virtual circle, a second virtual circle, and a third virtual circle. The first virtual circle has a first radius and a center located at a first distance to the longitudinal axis. The second virtual circle has a second radius and a center located at a second distance from the longitudinal axis. The second distance can be smaller than the first distance. The third virtual circle has a third radius that can be approximately equal to the first radius. The third virtual circle has its center located at a third distance to the longitudinal axis that can be approximately equal to the first distance to the longitudinal axis. In the expanded basket shape, the cloverleaf structure further can further define a height measured from a point on a perimeter of the second virtual circle to a neck directly away from the longitudinal axis in relation to the second virtual circle and between an adjacent first virtual circle and second virtual circle. The first radius, second radius, third radius, and height being configured to provide a lateral stiffness of the expandable basket assembly within a predetermined range. The method can further include forming a basket assembly for the medical probe such that the tubular frame provide structure support for the basket assembly, and such that the first radius, second radius, third radius, and height are configured to provide a lateral stiffness of the expandable basket assembly within a predetermined range.

The first radius can measure about 33% of the height. The second radius can measure about 39% of the height. The third radius can measure about 33% of the height. A minimum width of the sinusoidal-like member can measure about 25% of the height.

The first radius can measure between 31% and 35% of the height. The second radius can measure between 37% and 41% of the height. The third radius can measure between 31% and 35% of the height. A minimum width of the sinusoidal-like member can measure between 23% and 27% of the height.

The method can further include aligning the plurality of spines with a plurality of electrodes each having a lumen extending through the body of the electrode. The method can further include inserting each spine of the plurality of spines into the lumen of an electrode of the plurality of electrodes. The method can further include retaining the plurality of electrodes on the plurality of spines. Retaining the plurality of electrodes on the plurality of spines can include retaining an electrode of the plurality of electrodes with at least one biasing member.

The at least one biasing member can include a biasing member disposed outside of the lumen of the electrode. Additionally, or alternatively, the at least one biasing member can include a biasing member disposed inside the lumen of the electrode.

The method can further include positioning the spine of the expandable basket assembly through a lumen of an electrically insulative jacket of the plurality of electrically insulative jackets. The method can further include positioning a wire through the lumen of the electrically insulative jacket. The method can further include positioning an electrode of the plurality of electrodes over the electrically insulative jacket. The method can further include electrically connecting the wire to the electrode through an aperture in the electrically insulative jacket.

The method can further include covering a majority of the sinusoidal like member with the plurality of electrically insulative jackets. A distal portion of each of the plurality of electrically insulative jackets abuts the distal portion of an adjacent insulative jacket.

The method can further include covering a majority of an outer portion of the sinusoidal-like member with the plurality of electrically insulative jackets such that the outer portion of the sinusoidal-like member meanders around the first virtual circle and around the second virtual circle, and such that the outer portion is entirely positioned greater than the second distance from the longitudinal axis. An inner arc of the sinusoidal-like member can remain exposed to environment such that the inner arc meanders around the second virtual circle, and such that the inner arc is entirely positioned less than the second distance from the longitudinal axis. A distal portion of each of the plurality of electrically insulative jackets can taper outward and inward, following a curvature of the outer portion of the sinusoidal-like member.

Each respective spine of a plurality of spines can include a first electrode and a second electrode thereon. The method can further include aligning each respective spine of the plurality of spines with the first electrode and the second electrode. The method can further include inserting each respective spine of the plurality of spines into a lumen of the first electrode and a lumen of the second electrode. The method can further include fitting an end of each respective spine of the plurality of spines to the tubular shaft sized to traverse vasculature.

The method can further include offsetting the electrodes between adjacent spines along the longitudinal axis.

The electrode body lumen can be configured to receive the wire of the medical probe.

The wire can be insulated from the spine.

BRIEF DESCRIPTION OF THE DRAWINGS

FIG. 7A illustrates a perspective view of a distal end of a medical probe in an expanded form and including a coated distal end, in accordance with an embodiment of the present invention;

FIG. 7B illustrates the spine structure as formed from a tube stock and including a coated distal end;

FIG. 7C illustrates a perspective view of a distal end of a medical probe in an expanded form and including a coated distal end with a central opening, in accordance with an embodiment of the present invention;

FIG. 15A is a schematic pictorial illustration showing a side view of an irrigation hub, in accordance with the disclosed technology;

FIG. 15B is a schematic pictorial illustration showing a top view of an irrigation hub, in accordance with the disclosed technology;

FIG. 15C is a schematic pictorial illustration showing a bottom view of an irrigation hub, in accordance with the disclosed technology;

DETAILED DESCRIPTION

Figure 1:
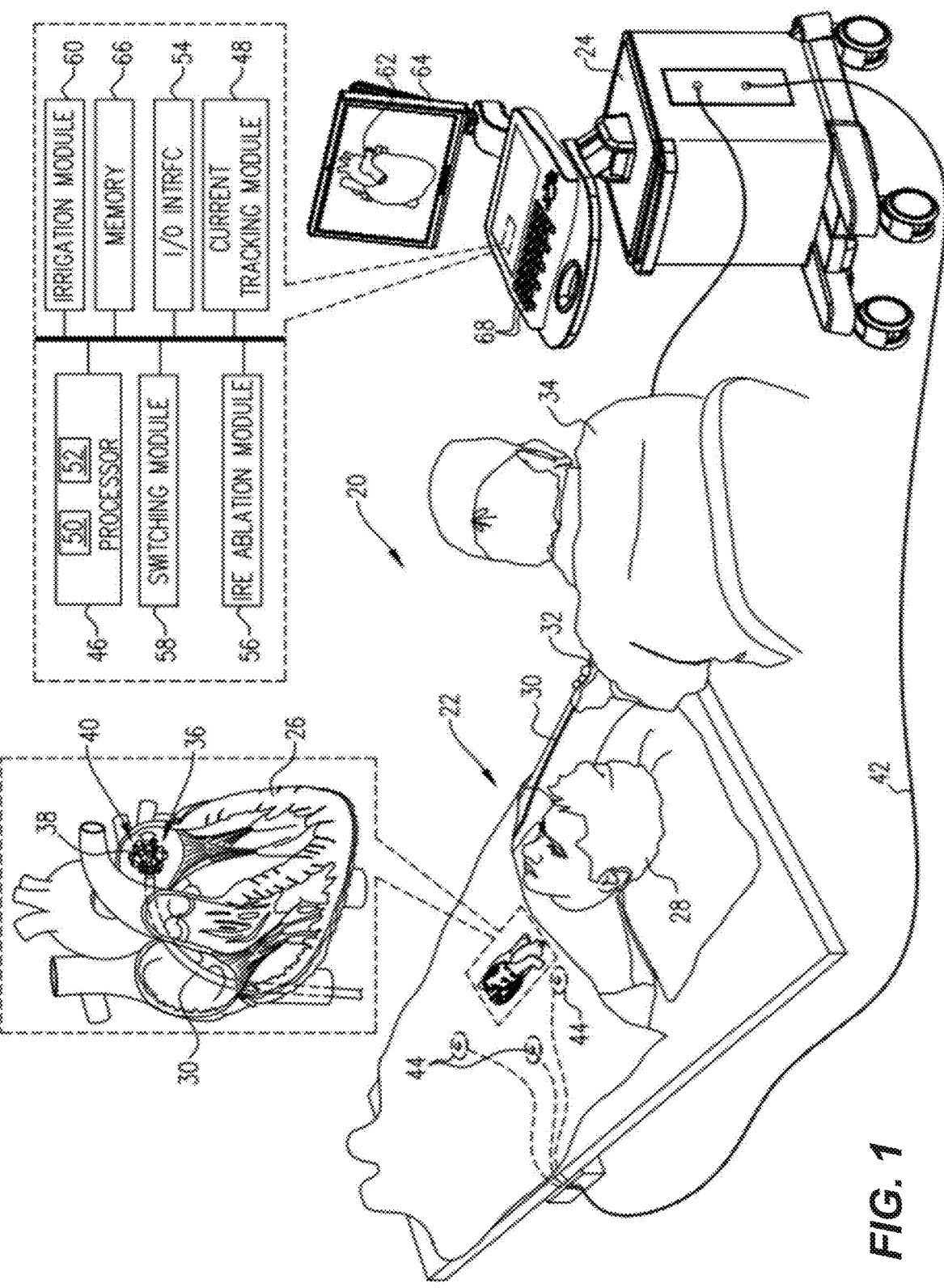
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

As used herein, the terms "patient," "host," "user." and "subject" refer to any human or animal subject and are not intended to limit the systems or methods to human use, although use of the subject invention in a human patient represents a preferred embodiment. In addition, vasculature of a "patient," "host." "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multielectrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial fibrillation ablation, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two or more electrodes that are both positioned at a treatment site; current density and electric flux density is typically approximately equal at each of the electrodes. "Unipolar" refers to ablation scheme utilizing a current path between two or more electrodes, wherein a first electrode or combination of electrodes experiences a high current density and high electric flux density and is positioned at a treatment site, and a second electrode or series of electrodes experiences comparatively lower current density and lower electric flux density and is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy, ultrasound, and/or a 3D mapping system utilizing magnetic and/or impedance based navigation.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of the myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversible, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the voltage applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the Appendix of priority Provisional Patent Application U.S. 63/477,404.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference and attached in the Appendix of priority Provisional Patent Application U.S. 63/477,404.

To deliver pulsed field ablation (PFA) in an IRE (irreversible electroporation) procedure, electrodes should contact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure. The unitary structure can include a plurality of linear spines formed from a planar sheet of material or tube stock and one or more electrodes coupled to each of the spines. The plurality of linear spines can converge at a central spine intersection including one or more cutouts. The cutouts can allow for bending of each spine such that the spines form an approximately spherical or oblate-spheroid basket assembly. It is noted that the cutouts (in various configurations described and illustrated in the specification) allows the basket to be compressed into a much smaller form factor when undeployed (or undergoing a retraction into a delivery sheath) without buckling or plastic deformation.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 approximate a distal end 39 of the medical probe 22. Basket assembly 38 can include a plurality of electrodes 40 affixed to a plurality of spines 214, as described in the description referencing FIGS. 2A, 2B, 2C, 3A, and 3B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 (disposed on an extension structure 38) engages cardiac tissue, the medical professional 34 can activate the medical probe 22 such that electrical pulses are delivered by the electrodes 40 to perform the IRE ablation.

Figure 2A:
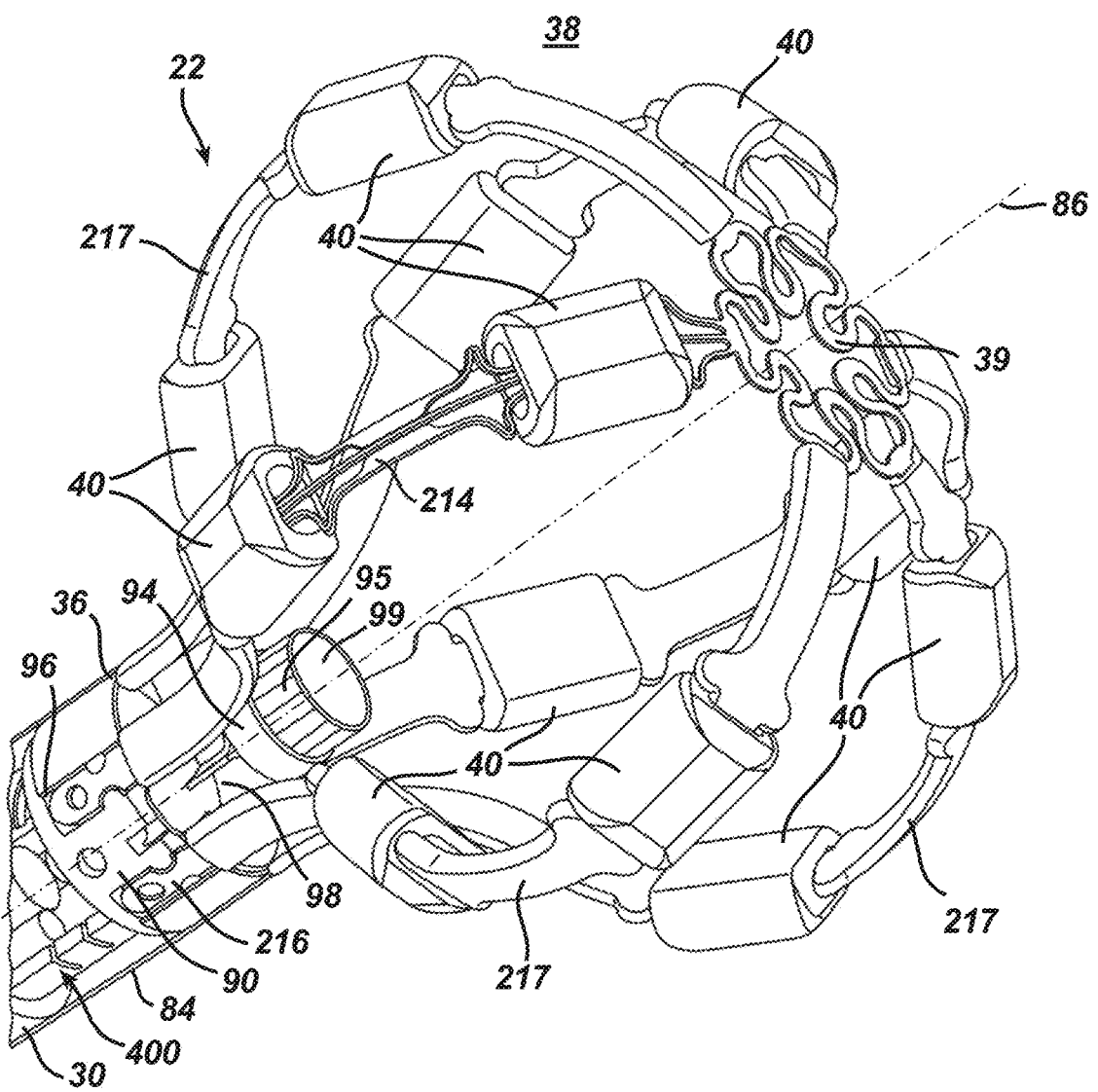
FIG. 2A is a perspective view of a medical probe in an expanded form, in accordance with an embodiment of the present invention.
Figure 2B:
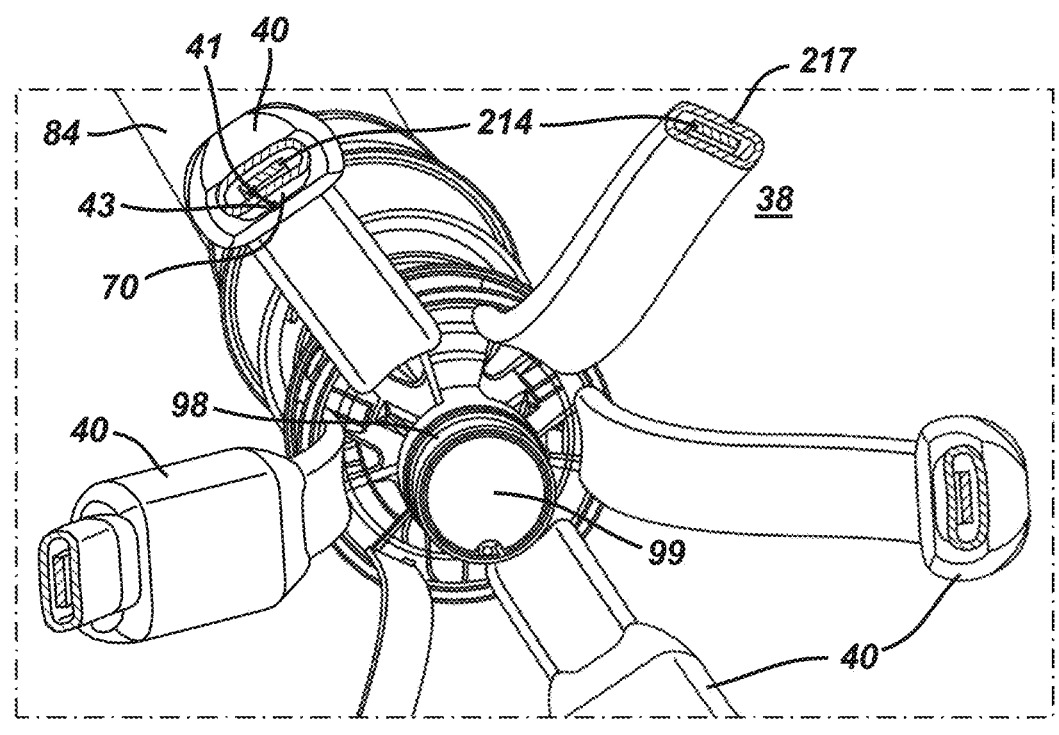
FIG. 2B is a sectional view of a cross-sectional plane orthogonal to the longitudinal axis to show the internal components of electrode and spine assembly.

The medical probe 22 can include a guide sheath and a therapeutic catheter, wherein the guide sheath includes the flexible insertion tube 30 and the handle 32 and the therapeutic catheter includes the basket assembly 38, electrodes 40, and a tubular shaft 84 (see FIGS. 2A through 2B). The therapeutic catheter is advanced through the guide sheath so that the basket assembly 38 is positioned in the heart 26. The distal end 36 of the medical probe 22 corresponds to a distal end of the guide sheath when the basket assembly 38 is contained within the flexible insertion tube 30, and the distal end 36 (of the tube 30) corresponds to a proximal portion (FIG. 2A) of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used for recording ECG signals or acting as location sensors during a medical procedure, electrodes 40 may perform other tasks such as ablating tissue in the heart.

As described hereinabove, in conjunction with tracking module 48, processor 46 may determine location coordinates of distal end 36 of tube 30 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and at least one skin patch.

In order to prevent blood coagulation, system 20 supplies irrigation fluid (e.g., a normal saline solution) to distal end 36 of tube 30 and to the proximal area of basket assembly 38. It is noted that irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

FIG. 2A is an illustration of a perspective view of a medical probe 22 including a basket assembly 38 in an expanded form when unconstrained, such as by being advanced out of an insertion tube lumen at a distal end 36 of an insertion tube 30. Probe 22 may include a contact force sensor 400 to determine contact force of the spines against cardiac tissues. Details of the contact force sensor are shown and described in US Patent Application Publication No. US2021/0077180A1 published Mar. 18, 2021, which disclosure is incorporated by reference herein.

It should be noted that the medical probe 22 illustrated in FIG. 2A lacks the guide sheath illustrated in FIG. 1. In the expanded form FIG. 2A, spines 214 bow radially outwardly and in the collapsed form (not shown) the spines 214 are arranged generally along a longitudinal axis 86 of insertion tube 30. In FIG. 2A, a plurality of electrically insulative jackets 217 is provided so that each jacket can be disposed between a respective spine 214 of the plurality of spines and a respective electrode 40 of the plurality of electrodes, thereby electrically isolating the plurality of electrodes from the plurality of spines.

Figure 3A:
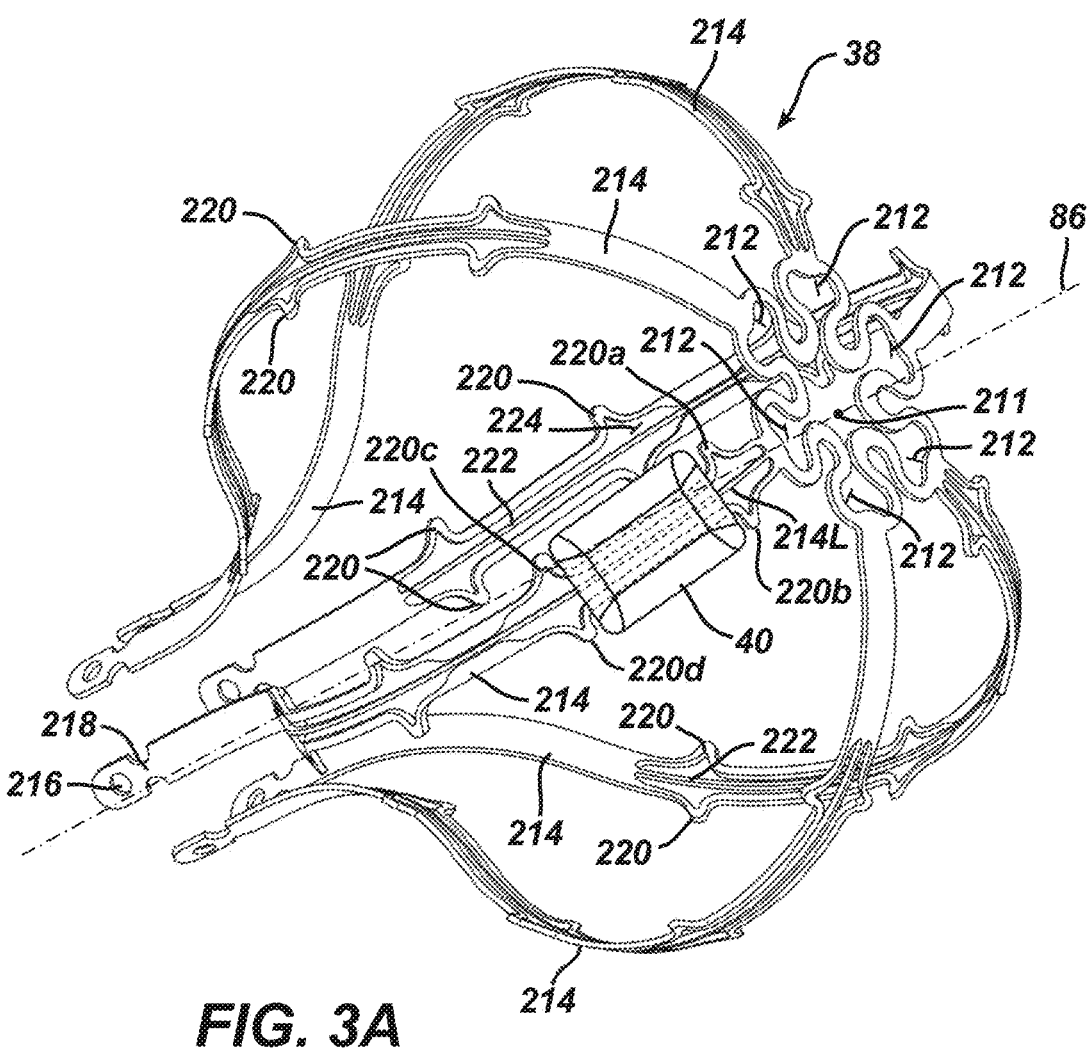
FIG. 3A illustrates the medical probe of FIG. 2A with only the underlying spine structure and one electrode disposed on one spine.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical e.g., circular, or rectangular that may appear to be flat cross-sections, and include a flexible, resilient material e.g., a shape-memory alloy such as nickel-titanium, also known as Nitinol forming a strut as will be described in greater detail herein. As shown in FIGS. 2A, 2B and 3A, basket assembly 38 has a proximal portion 36 and a distal end 39. The medical probe 22 can include a spine retention hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Turning to FIG. 3A, the plurality of flexible linear spines 214 converge at a central spine intersection 211 that is also disposed on a longitudinal axis 86 defined by the spines 214. In some examples central spine intersection 211 can include one or more cutouts 212 that allow for bending of the spines 214 when each spine respective attachment end 216 is connected to the spine retention hub 90, described in more detail below.

As shown herein, electrodes 40 positioned on spines 114 of basket assembly 38 can be configured to deliver ablation energy RF and/or IRE to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 i.e., toward the heart 26 tissue than inwardly.

Examples of materials ideally suited for forming electrodes 40 include gold, platinum and palladium and their respective alloys. These materials also have high thermal conductivity which allows the minimal heat generated on the tissue i.e., by the ablation energy delivered to the tissue to be conducted through the electrodes to the back side of the electrodes i.e., the portions of the electrodes on the inner sides of the spines, and then to the blood pool in heart 26.

Referring to FIG. 3A, basket assembly 38 of medical probe 22 is shown without the insulative sleeve 217 or associated wirings to electrodes 40 being disposed inside sleeve 217 to show the novel underlying basket structure 38. Basket 38 includes a single unitary structure that includes a plurality of spines 214 formed from a cylindrical tube stock (FIG. 3B) and treated to cause the spines 214 to bias radially outward. The material for the spine 214 can be selected from a group consisting of nitinol, cobalt chromium, stainless steel, titanium, and combinations hereof.

Referring to FIG. 2A, the spine retention hub 90 can be inserted into the tubular shaft 84 and attached to the tubular shaft 84. Spine retention hub 90 can include a cylindrical member 94 including a plurality of relief lands 96, multiple irrigation openings 98 to allow outflow of irrigation fluid into a volume defined by the basket spines, and hub end 99. Relief lands 96 can be disposed on the outer surface of cylindrical member 94 and configured to allow a portion of each spine 214, such as each spine attachment end 216, to be fitted into a respective relief land 96 of retention hub 90 also known as a coupler for a contact force sensor 400. The attachment end 216 can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly 38 is deployed. Reference electrode 95 can be disposed on the projection 94 or on the hub end surface 99. It should be noted that hub 90 in effect can have multiple functions: (1) to retain the spine legs proximally; (2) allow hub 90 (as well as the basket assembly 22) to be connected to distal tube 84; (3) to function as a fluid diverter for irrigation fluid delivered through distal tube 84; and (4) provide a reference electrode 95.

Referring to FIG. 2B, a sectional view of the basket assembly 38 is shown cut-away to show the spines 214 disposed inside jackets 217 with wiring 41 running along the spines 214 and extending through the jacket 217 to connect with the electrode 40 via connection point (e.g., solder pad) 43.

Figure 2C:
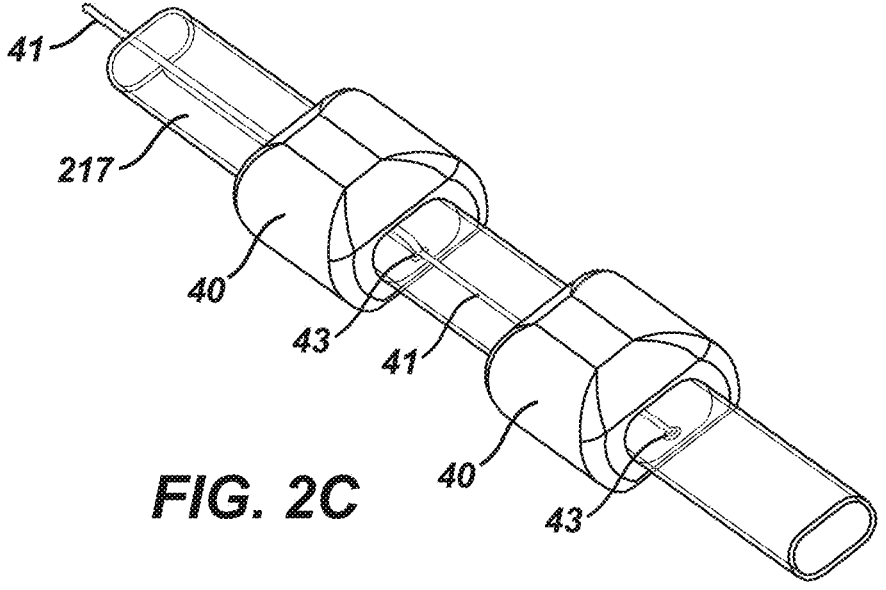
FIG. 2C is a perspective view of electrodes mounted on the insulative jacket with wires running along a spine for connection to each electrode.

FIG. 2C shows a perspective view of an opaque jacket 217 through which wirings 41 can be seen to extend through jacket 217 to respective connection points 43 of electrodes 40. It should be noted that the connection point 43 is not required to be disposed inside the lumen 70 of electrode 40 but can be outside lumen 70 as long as the connection point does not interfere with tissue contact of the electrode 40.

Figure 6A:
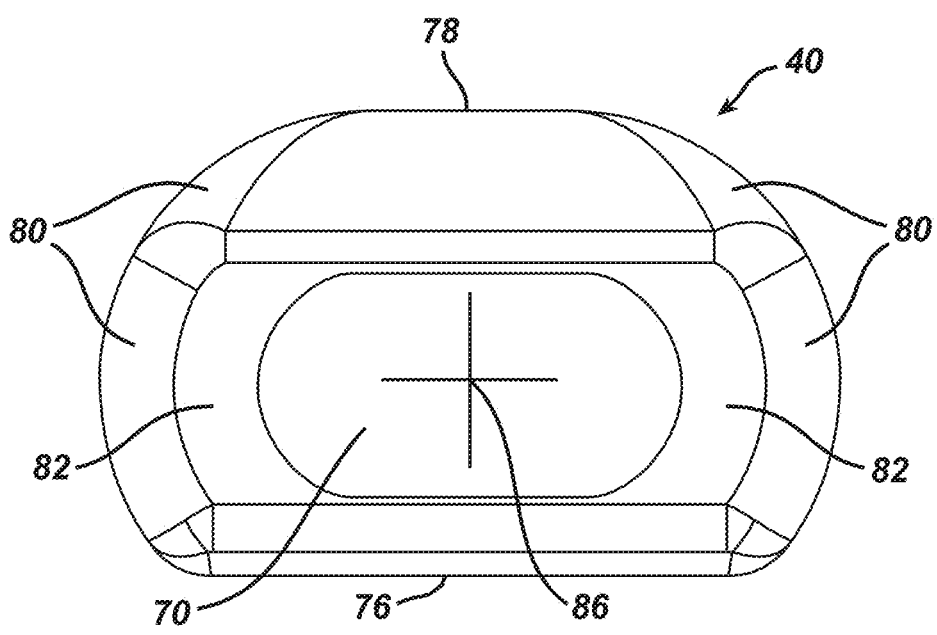
FIG. 6A and FIG. 6B illustrate a close-up view showing an electrode.
Figure 6B:
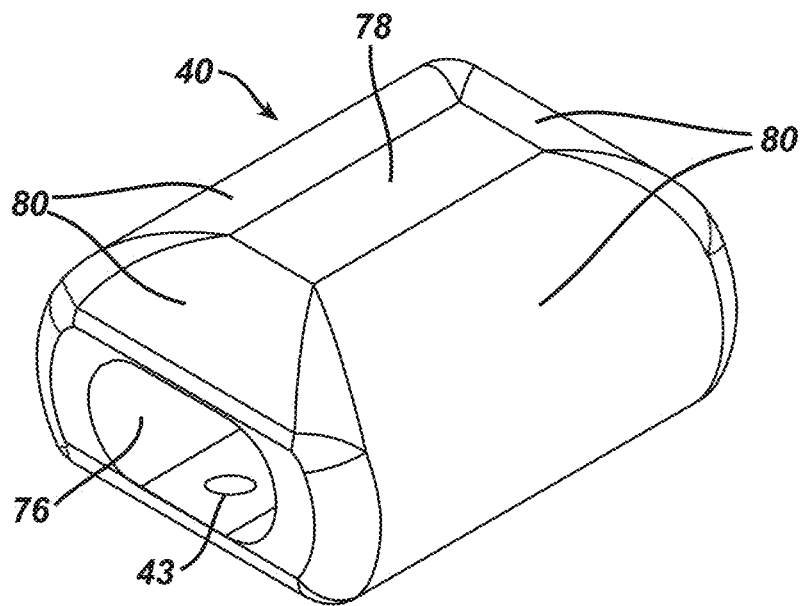

Referring to FIGS. 6A and 6B, in a preferred embodiment, electrode 40 is about 2 mm to about 3 mm long with a width from about 1.5 mm to about 2.5 mm wide and a height of about 0.8 mm to about 1.5 mm. The lumen 70 may have a negative surface area of about 0.4 mm-squared to about 0.7 mm-squared. The lumen 70 is not placed at the geometrical center but is rather offset lower so that the center 86 of lumen 70 is more towards the flat bottom surface 76. This arrangement ensures that more of the top surfaces 78 and 80 of electrode 40 is above the lumen 70 than below lumen 70.

Referring to FIG. 3A, electrode 40 can be located substantially in place with respect to spine 214 by way of a retention member 220 formed integrally with the spine 214. As illustrated in FIG. 3A, each of the spines 214 can include at least one retention member 220 extending generally transverse to the spine 214. To allow for insertion of the spine 214 through lumen 70 (FIG. 6A) of electrode 40, each spine 214 can be bisected with a central spine member 222 so that empty space 224 is provided to allow retention member 220 to bend inwardly towards the central spine member 222. The shape of retention member 220 can be of any shape as along as such shape serves to allow the member 220 to be compressed for insertion into lumen 70 of electrode 40 and once released to prevent movement of electrode 40 with respect to the retention member 220. In one embodiment, the at least one retention member 220 is shaped in a bow-like configuration with a center of such bow extending away from a periphery of spine 214. In a preferred embodiment, the at least one retention member 222 for each electrode 40 may include two bow shaped members 220 disposed in opposite direction and transverse to a longer length 214L of each spine 214.

In the configuration shown in FIG. 3A, the at least one retention member may have first 220a, 220b and second sets 220c, 220d of retention members 220 spaced apart along the spines. The first set includes two bow shaped members 220a. 220b disposed in opposite direction and transverse to a longer length 214L of each spine 214 and the second set includes two bow shaped members 220c, 220d disposed in opposite direction and transverse to a longer length 214L of each spine 214 so that each electrode 40 is captured between the first and second sets of retention members 220a, 220b and 220c and 220d.

Figure 3B:
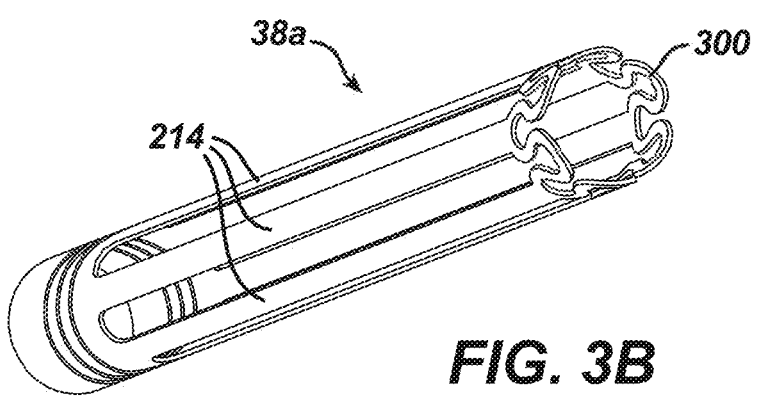
FIG. 3B illustrates the spine structure as formed from a tube stock.

FIG. 3B shows the spine structure 38a as formed from a tube stock. It is also within the scope of this invention for the spine structure 38a to be formed form a flat sheet stock, cut and heat treated to achieve the spheroidal basket shape shown herein. The spine structure 38a illustrated in FIG. 3B can be compressed longitudinally and the spines 214 can expand radially to form the basket shape spine structure illustrated in FIG. 3A of basket assembly 38 illustrated in FIG. 2A.

Figure 4A:
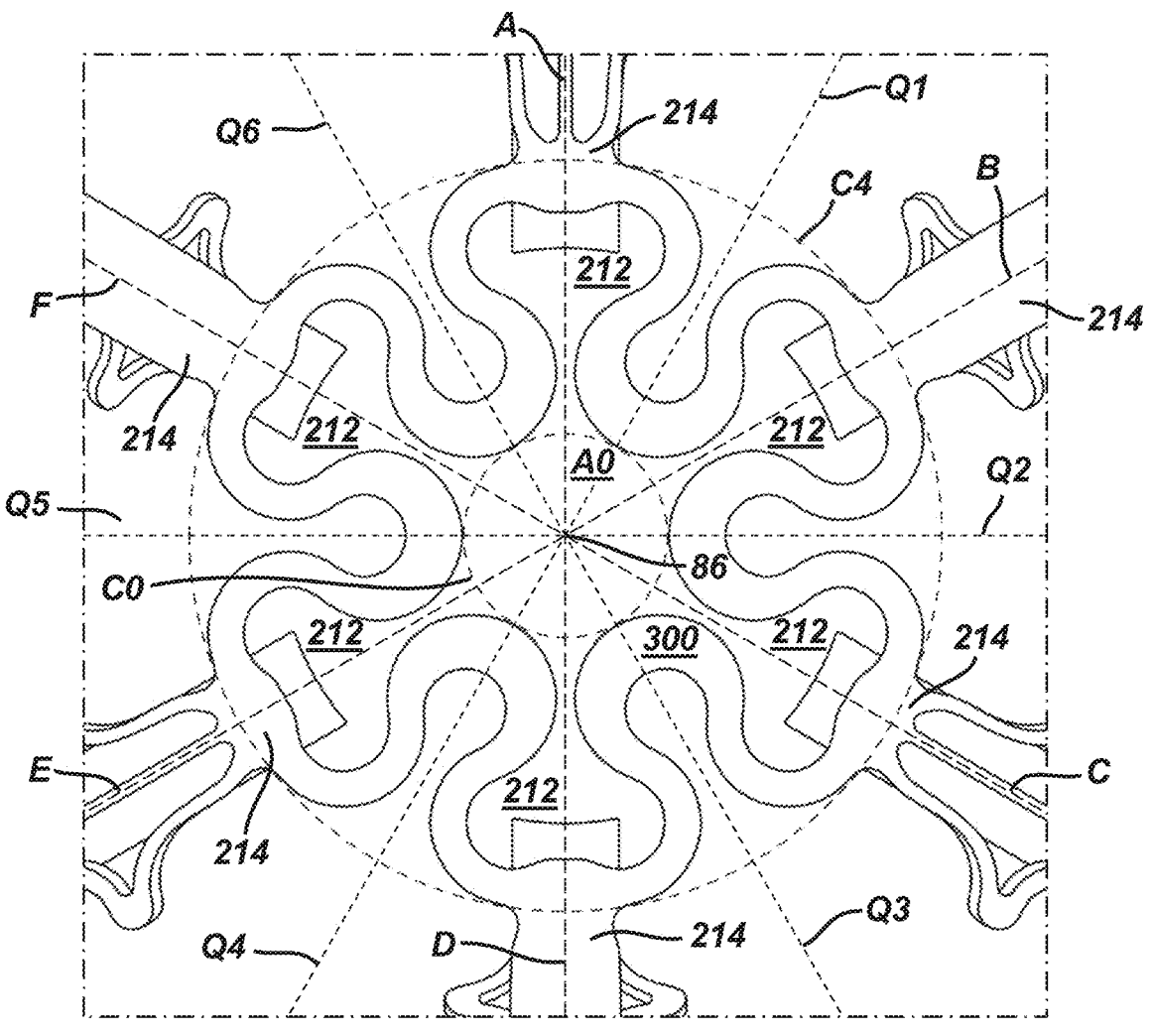
FIG. 4A illustrates an end and flattened view of the distal end of the basket spine structure of FIG. 3A as if the entire basket spines are captured flat between two flat plates of glass for viewing by an observer located on the longitudinal axis.
Figure 4B:
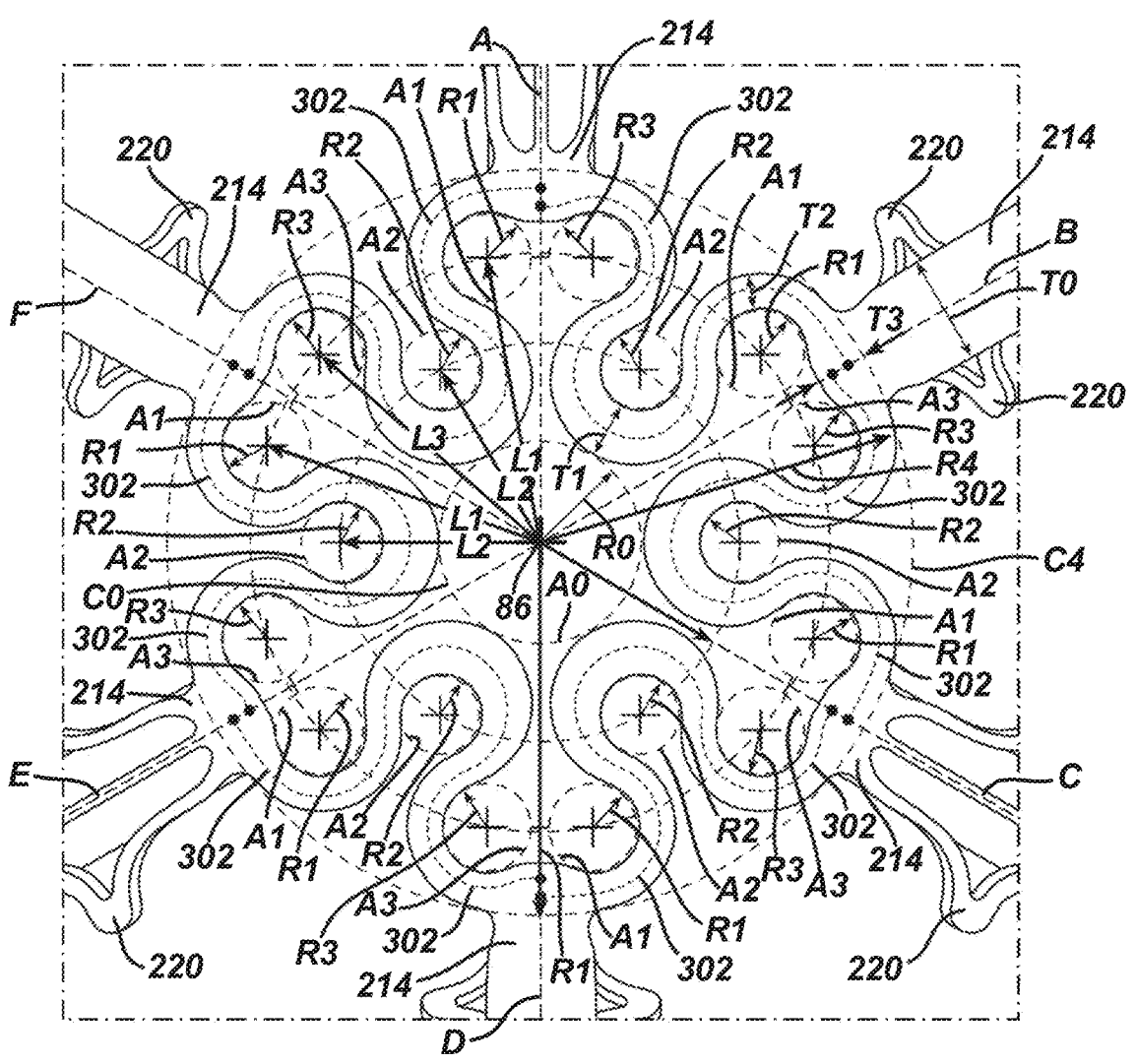
FIG. 4B illustrates the end view of the spine structure of FIG. 4A with design nomenclatures of a cloverleaf structure disposed proximate the distal end of the spine structure of FIG. 3A.

FIGS. 4A and 4B show the distal portion 39 (FIG. 2A) in which the distal portion 39 of basket assembly 38 of medical probe 22 can be considered as being flattened between two flat sheets of glass. In this viewing configuration, it can be seen in FIG. 4A that distal portion 39 defines a structure 300 resembling a cloverleaf and hence structure 300 will be referred hereafter as a "cloverleaf". As before, basket 38 in FIG. 4A and FIG. 4B has a plurality of spines 214 extending along the longitudinal axis 86 from a proximal central proximal spine portion 36 to a distal spine portion 39.

In FIG. 4A, the distal spine portion 39 defines a cloverleaf structure FIG. 4A, 300 disposed radially around the longitudinal axis 86. Each clover cutout 212 is aligned along radial axis A, B, C, D, E and F extending orthogonally from axis 86 so that the plurality of spines 214 extend from the proximal central spine portion 36 in an equiangular pattern such that respective angles between respectively adjacent spines are approximately equal. While the preferred embodiment includes six spines, it is within the scope of the invention to have any number of spines from four to twelve.

Of note is that the cloverleaf structure 300 also defines a central cutout CO with a negative or empty area A0 disposed about the longitudinal axis 86. In particular, the cloverleaf structure 300 can be delineated by the following structures: a sinusoidal-like cloverleaf member 300 extending from one spine 214 to an adjacent spine 214 in a direction e.g., counterclockwise, or clockwise around the longitudinal axis 86. This characteristic of the sinusoidal structure 300 can be seen in FIG. 4B with for example, spine 214 located on radial axis A. Starting from this spine 214 on axis A, a sinusoidal-like cloverleaf member 300 is configured so that it meanders as indicated by dashed line 302 around a portion of the cutout 212 having a negative or open first area A1 which can be approximated by circle R1. As used herein, the term "open area" means the absence of any solid structure to define an empty space. This first open area A1 is approximately 20% that of the central area A0. For convenience, the first open area A1 can be approximated by the first virtual circle R1 that has its center located at a first distance L1 to the longitudinal axis 86. Continuing in FIG. 4B, the sinusoidal cloverleaf member 300 meanders in a couter-clockwise direction from axis A to axis F around a second open area A2 towards an adjacent spine 214 located on axis F. For convenience, the second open area A2 can also be approximated to a second virtual circle R2 having a second open area A2 of approximately 90% of the first open area A1. It is noted that the second virtual circle may have its center of radius R2 located at a second distance L2 smaller than the first distance L1 to the longitudinal axis 86. Continuing towards axis F in FIG. 4B, the sinusoidal cloverleaf member 300 meanders dashed line 302 around a third open area A3 which for convenience is approximated by third virtual circle with radius R3. The third virtual circle has its center for radius R3 located at a third distance L3 to the central axis 86 that is greater than L2 and approximately equal to the first distance L1. Once the sinusoidal cloverleaf member 300 crosses axis F, the structural nomenclatures repeat again with another first open area A1 on the other side of axis F closer to axis E on which sinusoidal cloverleaf member 300 meanders as referenced by dashed line 302 towards next spine 214 located on axis E.

In FIG. 4B, a width TO of the spine 214 can be from 0.25 to 1 mm while the sinusoidal member 302 has a maximum width T1 of about ½ of the width of TO with a minimum width T2 of about ⅓ of spine width TO. A width T3 proximate the spine axis (A, B, C, D, E or F) is about the same as the maximum with T1. The central area A0, approximated by radius R0, is approximately 0.8 mm-squared, the fourth virtual circle C4 may have an area approximately 14 times greater than the central area A0. Each of the first and third virtual circle R1 and R3 is located at a first distance L1 of approximately 1.5 mm from the central axis 86 while the second virtual circle R2 is located at a distance L2 of approximately ½ that of the first distance L1.

Preferably, the plurality of spines 214 can be made from a material selected from a group consisting of nitinol, cobalt chromium, stainless steel, titanium, and combinations or alloys hereof. Each electrode 40 can be made of a material selected from stainless steel, cobalt chromium, gold, platinum, palladium, and alloys or combinations hereof.

The inventors have devised the cloverleaf structure 300 in order to allow the basket assembly 38 to be compressed from a maximum diameter of the basket of approximately 12 mm to fit within an 8-12 French sheath without buckling or causing permanent plastic deformation to the spines 214 at any part of the basket assembly 38. In an alternative embodiment, if the number of spines is increased the size of the sheath may be increased to up to 14.5 French to accommodate the additional spines. By virtue of this design, the inventors have been able to compress the basket into a sheath and deploy for full expansion for at least 40 times without any physical sign of buckling.

Referring back to FIG. 4A, it is noted that the sinusoidal-like cloverleaf member 300 is configured so that a portion of cloverleaf member 300 is tangential to the central circle CO proximate a location between any two radial axes on which two neighboring spines 214 are located. For example, with spine 214 on radii axis A neighboring spine 214 on axis B, the sinusoidal cloverleaf member 300 is tangential to the open circle CO at a location bisecting the two radial axis A and B by a line Q1 connected to the central axis 86. This tangential characteristic of the sinusoidal cloverleaf member 300 around the open area A0 is repeated for any two adjacent spines 214 as spine 214 on axis B and spine 214 on axis C and so on for all of the bisecting axes Q1, Q2, Q3, Q4, Q5, Q6. The bisecting axes Q1, Q2, Q3, Q4 correspond to peaks of the sinusoidal cloverleaf member 300 and the radial axes A, B, C, D, E, F correspond to troughs of the sinusoidal cloverleaf, wherein peaks of the sinusoidal member are closer to the central axis 86 and troughs are further from the central axis 86.

Figures 5A, 5B:
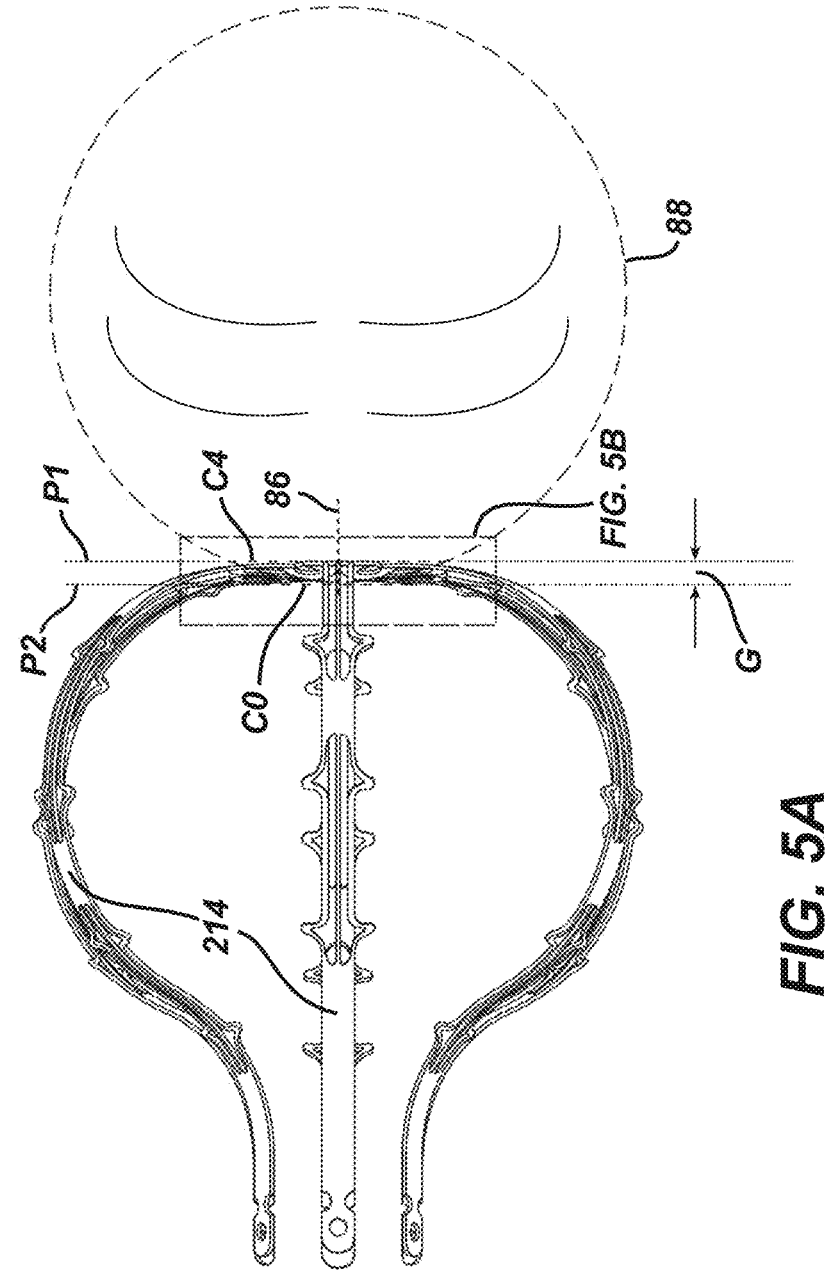
FIG. 5A illustrates a side view of the basket spine structure of FIG. 3A to illustrate a concavity of the cloverleaf structure that can be approximated by a virtual sphere.
FIG. 5B is a close-up of the inset shown in FIG. 5A to show the concavity of the distal central portion of basket assembly 38.
Figure 5B:
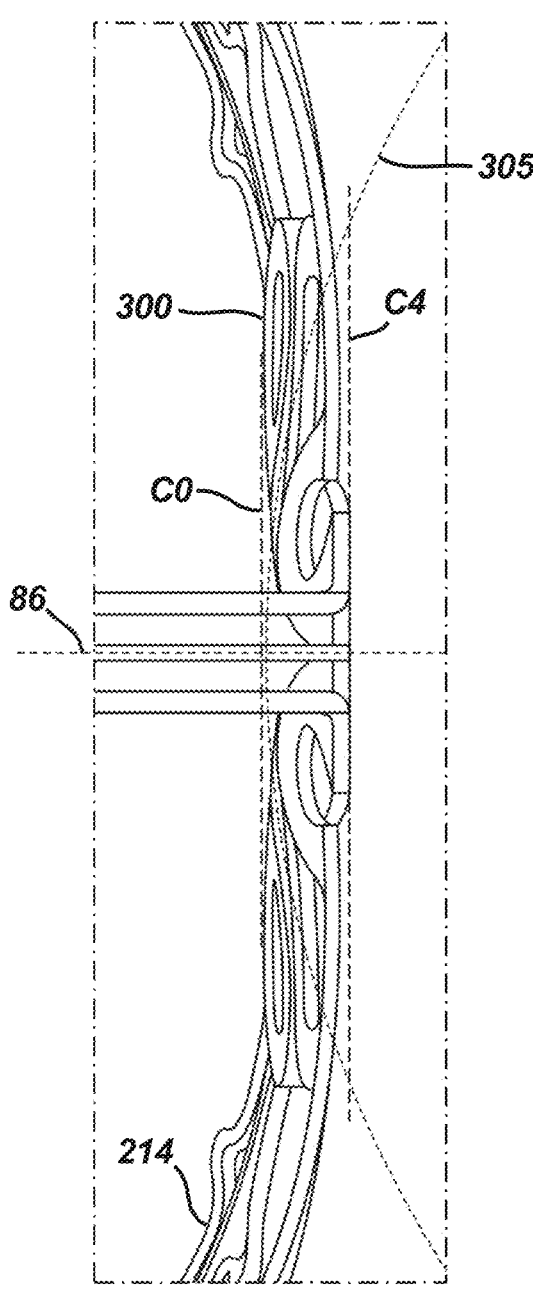

Another notable feature of the basket structure 38 is a concavity 305 of the distal central portion 211 (FIG. 3A) that can be seen with reference to FIGS. 5A and 5B. In FIG. 5A, it can be seen that the cloverleaf structure 300 is bent so that its open center 211 is contiguous to a plane defined by central circle CO and spaced apart by a gap G with respect to a plane defined by the fourth virtual circle C4 encircling the cloverleaf structure 300. The concavity is indicated by a virtual circle 88 and a dashed line 305 representing the compound curvature generated by the cloverleaf structure 300 about the central axis 86.

FIG. 6A illustrates the electrode 40 an end front view and FIG. 6B illustrates the same electrode from a top-down perspective view of electrode 40, in accordance with an embodiment of the present invention. Each electrode 40 is fabricated from a biocompatible electrically conductive material, such as stainless steel, cobalt chromium, platinum, palladium, iridium or gold and alloys or combinations of such metals. Each end (one shown in FIG. 6A) of electrode 40 is provided with generally flat lands 82 surrounding a lumen 70 with curved outer surfaces 80 surrounding the lands 82. Electrode 40 has a tissue facing surface with a generally flat top surface 78 with curved outer perimeter 80 surrounding the generally flat top surface 78. The lumen 70 (i.e., a hollow through opening) extends along longitudinal axis 86 therethrough. In addition to the tissue contacting outer surface, each given electrode 40 has an inner surface 76 defined by its lumen 70 on which spine 214 can be inserted through the lumen 70. Electrical wire or electrical trace 41 (FIG. 2C, sufficiently sized to deliver current pulses of at least 10 amps) can be connected to a connection point on the electrode (outside or inside surface). Preferably, wire 41 is electrically connected to a connection point 43 on the inside surface 76 of lumen 70. The cross-section of the electrode can be ovoid, trapezoidal, or substantially ovoid or trapezoidal shape as shown in FIGS. 6A and 6B.

Figures 7A, 7B, 7C:
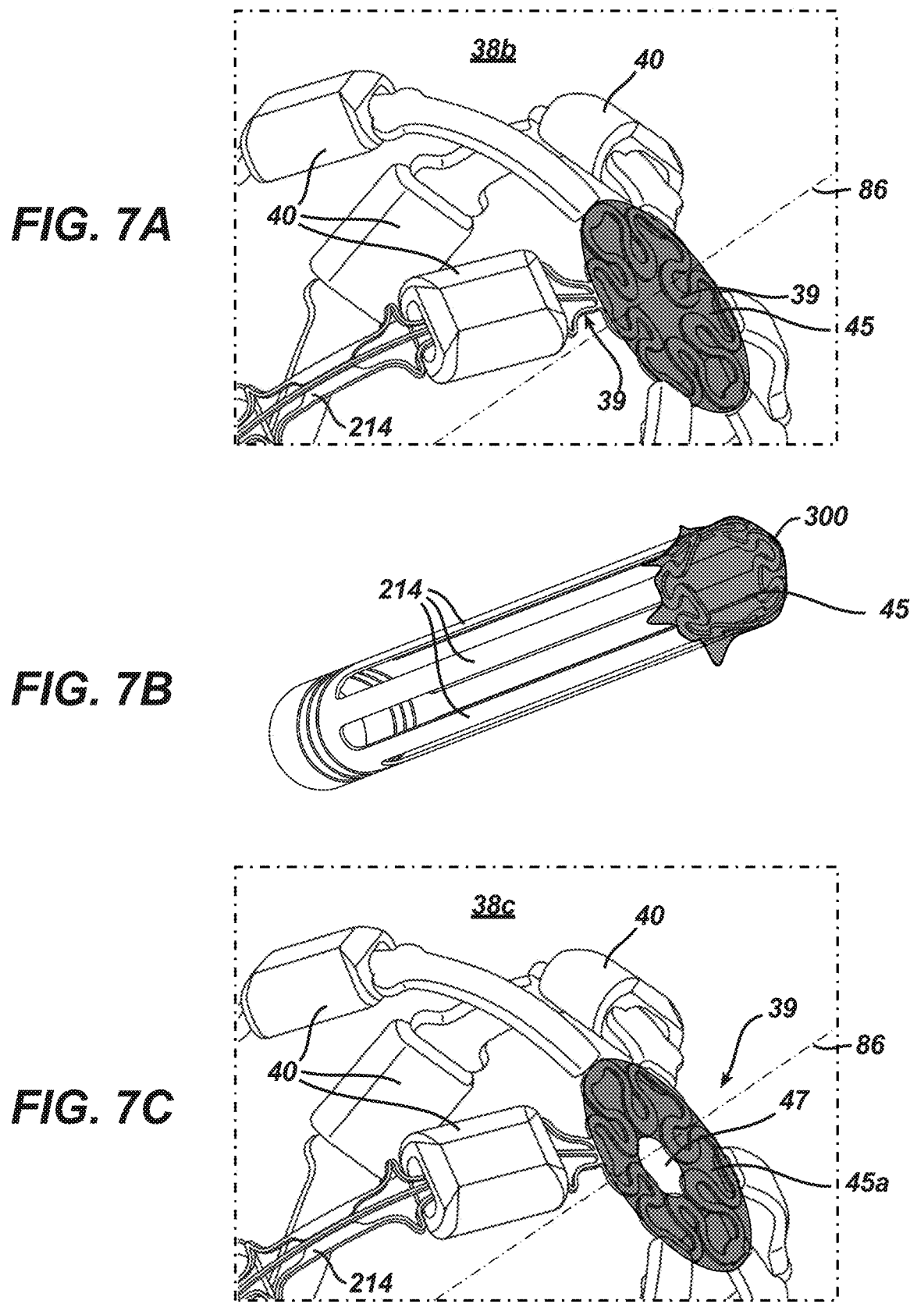

FIG. 7A is a perspective view of another example basket assembly 38b of a medical probe in an expanded form and including a coated distal end 39. The distal end 39 includes an atraumatic coating 45 configured to reduce likelihood of tissue damage due to pressure of the distal end 39 of the basket assembly 38b against tissue. The coating 45 covers the sinusoidal-like member 300 and covers the central cutout A0 circumscribed by the sinusoidal-like member 300. The coating 45 can be applied to alternative configurations of basket assembly 38b as understood by one skilled in the art to reduce likelihood of tissue damage due to pressure of the distal end 39 of the basket assembly 38b against tissue. The coating 45 may be particularly suited for basket assembly structures having an open distal end. The coating 45 may also be particularly suited for basket assembly structures having struts or structures with edges positioned at the distal end of the basket assembly. Additionally, the coating 45 serves to electrically isolate some or all of spines 214, which allows electrodes 40 to be placed more distally than would otherwise be the case as electrodes need to be spaced away from exposed conductive surfaces to avoid arcing.

FIG. 7B illustrates the spine structure as formed from a tube stock and including the coating 45 at the distal end. The coating 45 preferably includes a polymeric material. The coating 45 can be applied to the basket assembly 38b by dipping the distal end 39 in a liquid polymer and curing the polymer to form a flexible membrane. The distal end 39 can be dipped when the basket assembly is in an expanded form as illustrated in FIG. 7A, when the basket assembly is collapsed to a tubular shape similar to as illustrated in FIG. 7B, or at a partially expanded state between the states illustrated in FIGS. 7A and 7B. The distal end 39 can be expanded to the expanded form as illustrated in FIG. 7A as the coating 45 is cured to take its final shape.

FIG. 7C illustrates a perspective view of a distal end 39 of another example basket assembly 38c of the medical probe in an expanded form and including a coating 45a with a central opening 47. The central opening 47 may allow for the basket assembly 38c to be easier to collapse compared to the coating 45 illustrated in FIGS. 7A and 7B.

Figure 8A:
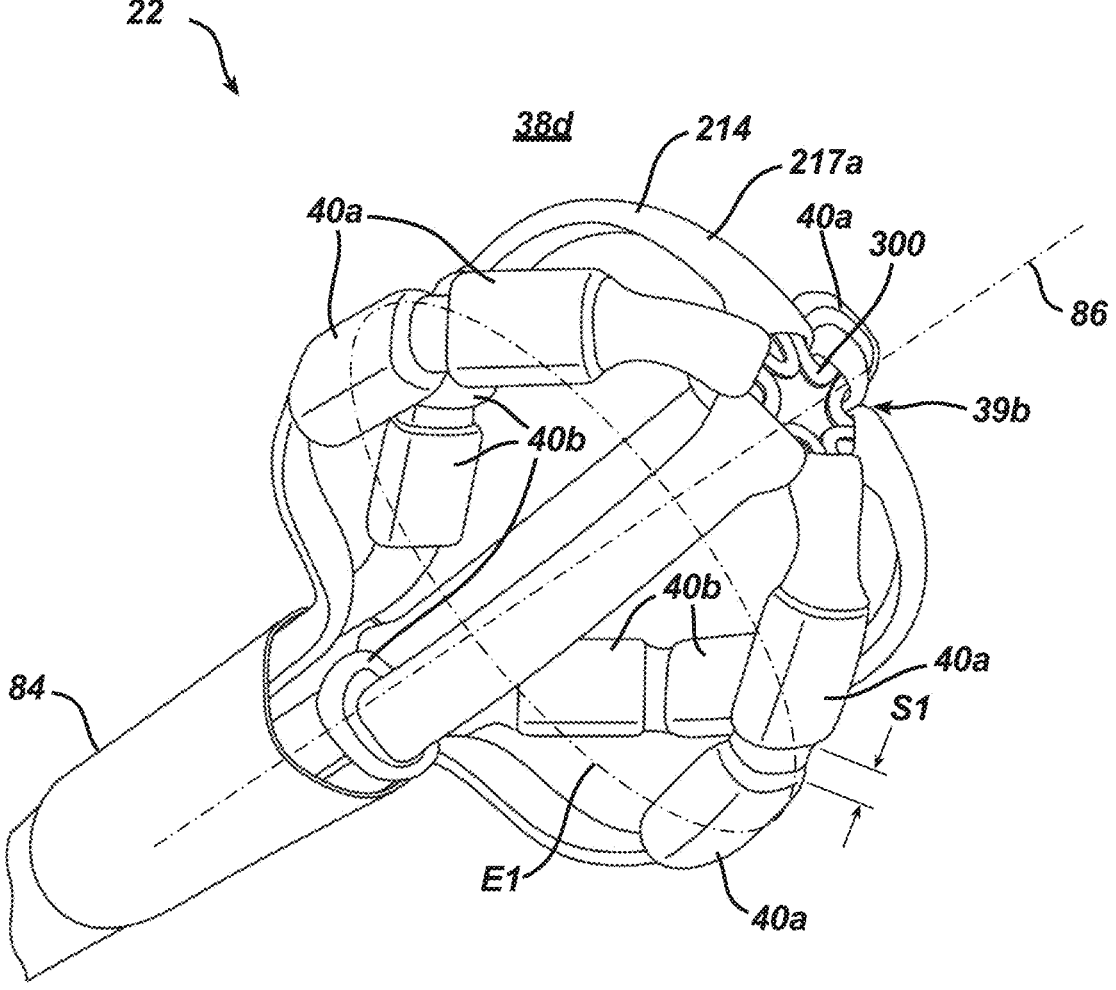
FIG. 8A illustrates a perspective view of a medical probe including closely spaced electrode pairs and a jacket extending over a portion of a distal cloverleaf structure.

FIG. 8A illustrates a perspective view of medical probe 22 having an example basket assembly 38d including spines 214 each including a closely spaced electrode pair 40a, 40b and a jacket 217a extending over a proximal portion 306 (FIG. 10) of the cloverleaf 300. Electrodes of each electrode pair 40a, 40b have an edge-to-edge spacing S1 between electrodes in the pair. Electrode pairs 40a, 40b are positioned in an alternating pattern with more distally positioned electrode pairs 40a on every other spine 214, and more proximally positioned electrode pairs 40b positioned on every other spine 214. The basket assembly 38b defines an equator E1 perpendicular to the longitudinal axis 86 where the circumference of the basket shape is the greatest. The proximal electrode pairs 40b are entirely proximal of the equator E1. The equator E1 traverses a proximal electrode of each of the distal electrode pairs 40a.

Figure 8B:
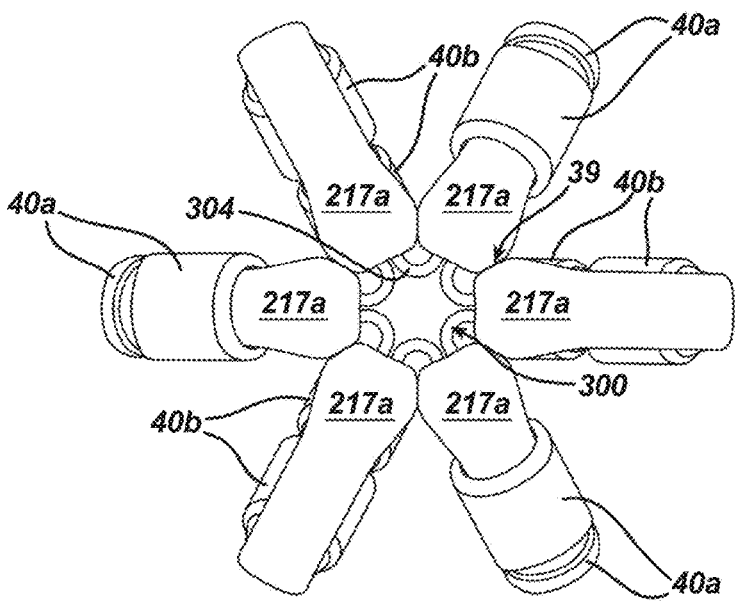
FIG. 8B illustrates a distal end view of the medical probe illustrated in FIG. 8A.
Figure 10:
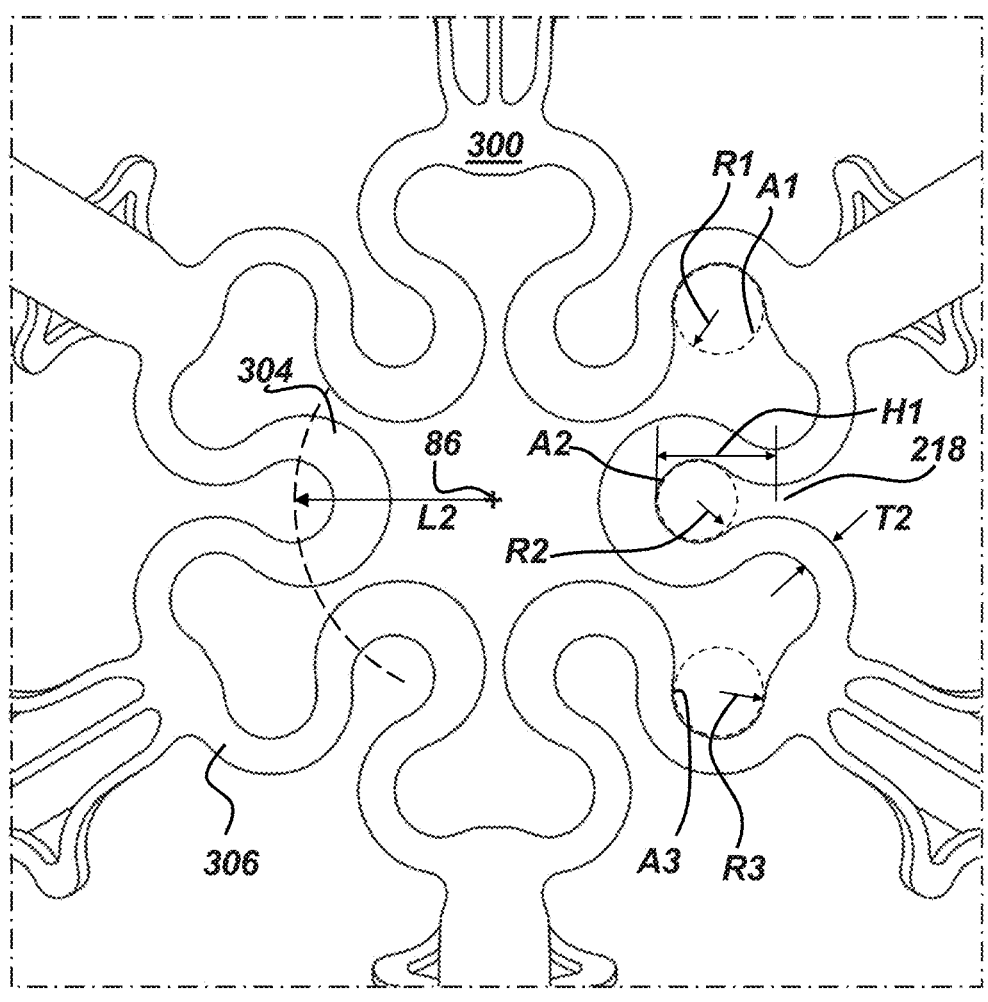
FIG. 10 illustrates selected dimension of the cloverleaf structure which are tailored to achieve desired mechanical properties of the spine basket structure.

FIG. 8B illustrates a distal end view of the basket assembly 38d illustrated in FIG. 8A. Inner arcs 304 of the cloverleaf 300 are exposed while an outer portion 306 (FIG. 10) of the cloverleaf 300 is covered by the jackets 217a to provide an atraumatic distal end 39 of the basket assembly 38d. The inner arcs 304 and covered outer portion 306 of the cloverleaf 300 are indicated in FIG. 10. The second length L2 from the longitudinal axis L-L to the center of the second virtual circle A2 (FIG. 4B) defines a boundary between the inner arcs 304 and the outer portion 306 of the cloverleaf 300. A majority of each outer portion 306 (FIG. 10) is covered by a respective jacket 217a. A majority of the inner arcs 304 are exposed to environment. A distal portion of each jacket 217a tapers outward and inward, following the curvatures of the respective proximal portion 306 (FIG. 10) of the cloverleaf 300 covered by the jacket 271a. The distal portions of each jacket 217a abut each other at the distal end 39 of the basket assembly 38d when the basket assembly is expanded. The distal ends of the jackets 271a can be heat set closed and/or thermally fused. Additionally, or alternatively, a small amount of polymer adhesive or epoxy can be applied to the distal ends of each jacket 217a to seal the jacket 217a to the spine 214.

Figure 8C:
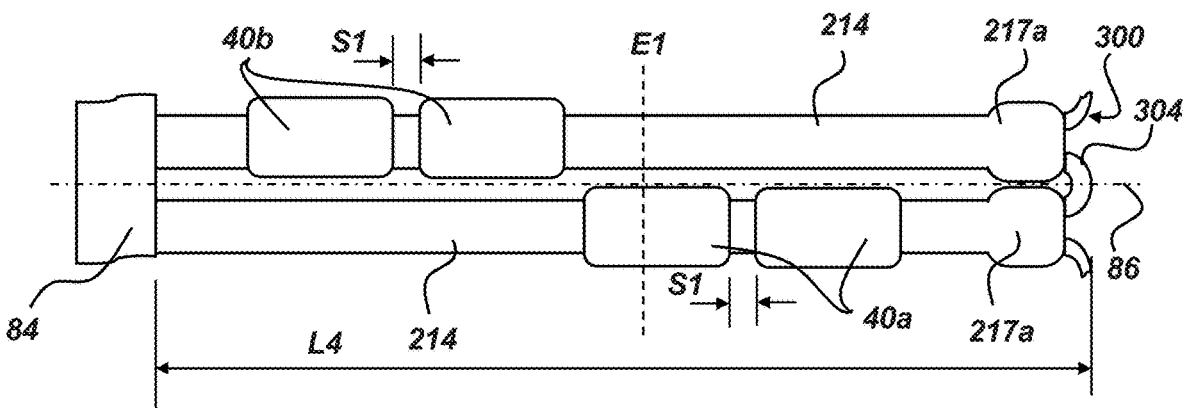
FIG. 8C illustrates a side view of two adjacent spines of the medical probe illustrated in FIG. 8A in a collapsed form for delivery.

FIG. 8C illustrates a side view of two adjacent spines 214 of the basket assembly 38d illustrated in FIG. 8A in a collapsed form for delivery. Only two spines 214 are illustrated for the sake of simplicity of illustration. Each spine 214 has a length L4 measured from a distal end of the shaft 84 to a distal end of the cloverleaf 300, at the peak of the distal arc 304. The equator E1 is positioned approximately at a midpoint of the length L4 of the spines 214. The electrode pairs 40a. 40b are positioned such that electrode pairs 40a, 40b on adjacent spines 214 do not overlap along the length L4 of the spine 214. Electrodes of distal electrode pairs 40a are entirely distal of electrodes of the proximal electrode pairs 40b when the basket assembly 38d is collapsed for delivery.

Figure 9:
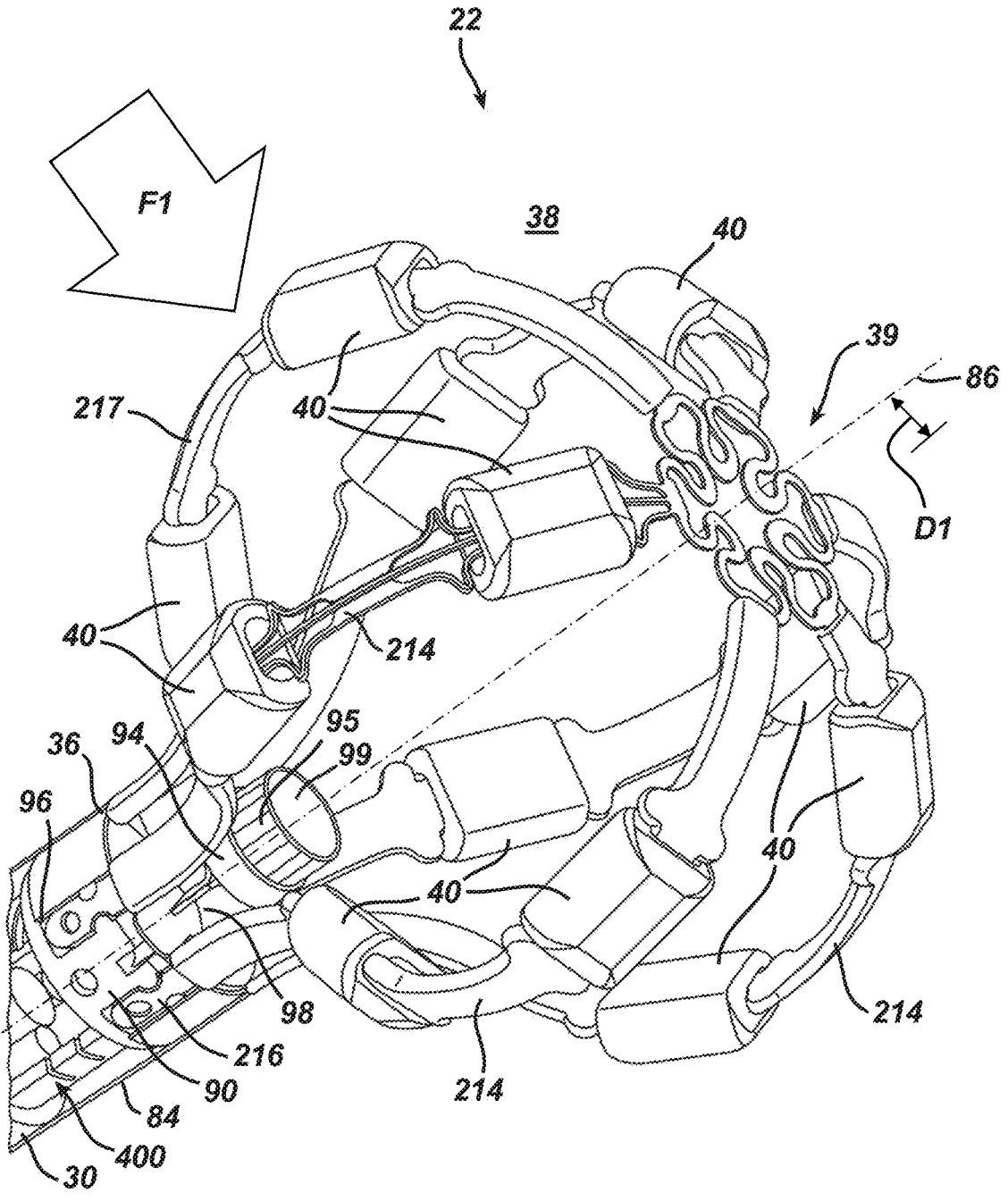
FIG. 9 illustrates a perspective view of a medical probe experiencing a lateral force and a resulting lateral displacement.

FIG. 9 illustrates a perspective view of a medical probe 22 experiencing a lateral force F1 and a resulting lateral displacement D1. The amount of lateral displacement D1 for a given force F1 defines a lateral stiffness of the basket 38. The less the displacement D1, the greater the stiffness. A desired lateral stiffness can be determined based on qualitative feedback from physicians or other users of the medical probe 22.

FIG. 10 illustrates selected dimension of the cloverleaf structure 300 which can be tailored to achieve desired mechanical properties of the basket assembly 38. Radius R1 of the first open area A1, radius R2 of the second open area A2, radius R3 of the third open area A3, and minimum width T2 of the sinusoidal member 302 can each be adjusted to achieve desired mechanical properties. These dimensions are also illustrated in FIG. 4B. Additionally, a height H1 can be adjusted to achieve desired mechanical properties. The height H1 is measured from an innermost point of the second open area A2 to a neck 218 directly radially outward, away from the longitudinal axis L-L, from the second open area A2. The neck 218 is positioned where adjacent proximal portions 306 of the cloverleaf structure 300 are closest to each other. The minimum width T2 can be positioned near a perimeter of the sinusoidal member 302.

The three radii R1, R2, R3, the height H1, and the width T2 can be given acceptable ranges based on geometry. The acceptable ranges can be determined based on manufacturability (e.g. ability to cut from a tube or sheet), overall size of the cloverleaf structure 300, etc. The thickness of the tube or sheet can be given acceptable ranges based on geometry and desired mechanical properties. A desired curvature indicated by virtual circle 88 in FIG. 5A and/or complex curve 305 in FIG. 5B may also be considered. The virtual circle 88 can be achieved if the spines are cut from a tube or a sheet.

The mechanical properties considered can include lateral stiffness as illustrated in FIG. 9 and peak stress observed during retraction of the basket assembly 38 into a sheath or intermediate catheter. A range of acceptable lateral stiffness can be predetermined (e.g. based on qualitative physician feedback), and a maximum peak strain during retraction of the basket assembly 38 can be predetermined to ensure the basket assembly does not plastically deform. The first radius R1, second radius R2, third radius R3, and height H1 can be configured to provide a lateral stiffness of the expandable basket assembly within a predetermined range. The first radius R1, second radius R2, third radius R3, and height H1 can be configured to provide a maximum peak strain during retraction of the expandable basket assembly into an intermediate catheter such that the maximum peak stress is less than a predetermined threshold. The maximum peak stress can be determined based on a peak von Mises stress during sheath insertion or retraction. Several acceptable combinations of dimensional variables (R1, R2, R3, H1, T2) illustrated in FIG. 10 can be identified as resulting in a basket assembly 38 having lateral stiffness and peak stress during retraction within an acceptable range. Alternatively, or additionally, any combination of any suitable dimensions illustrated in FIG. 4B and/or FIG. 10 can be varied to result in a basket assembly having a lateral stiffness and/or maximum peak stress during retraction within an acceptable range.

Other mechanical properties or geometrical considerations can further be taken into account when selecting dimensional variables for the basket assembly.

In one embodiment, the first radius R1 and the third radius R3 each measure about 0.008 inches; the second radius R2 measures about 0.0095 inches; the height H1 measures about 0.0244 inches; and the width T2 measures about 0.006 inches. In one embodiment, the first radius R1 and the third radius R3 each measure about 33% of the height H1, the second radius R2 measures about 39% of the height, and the width T2 measures about 25% of the height H1. The width T2 is a minimum width of the sinusoidal-like member. The thickness of the tube or sheet from which the spines 214 and cloverleaf structure 300 are cut can have a thickness of approximately 0.004 inches, so that the resulting spines 214 and cloverleaf structure 300 have a thickness of approximately 0.004 inches.

Figures 11A, 11B, 11C:
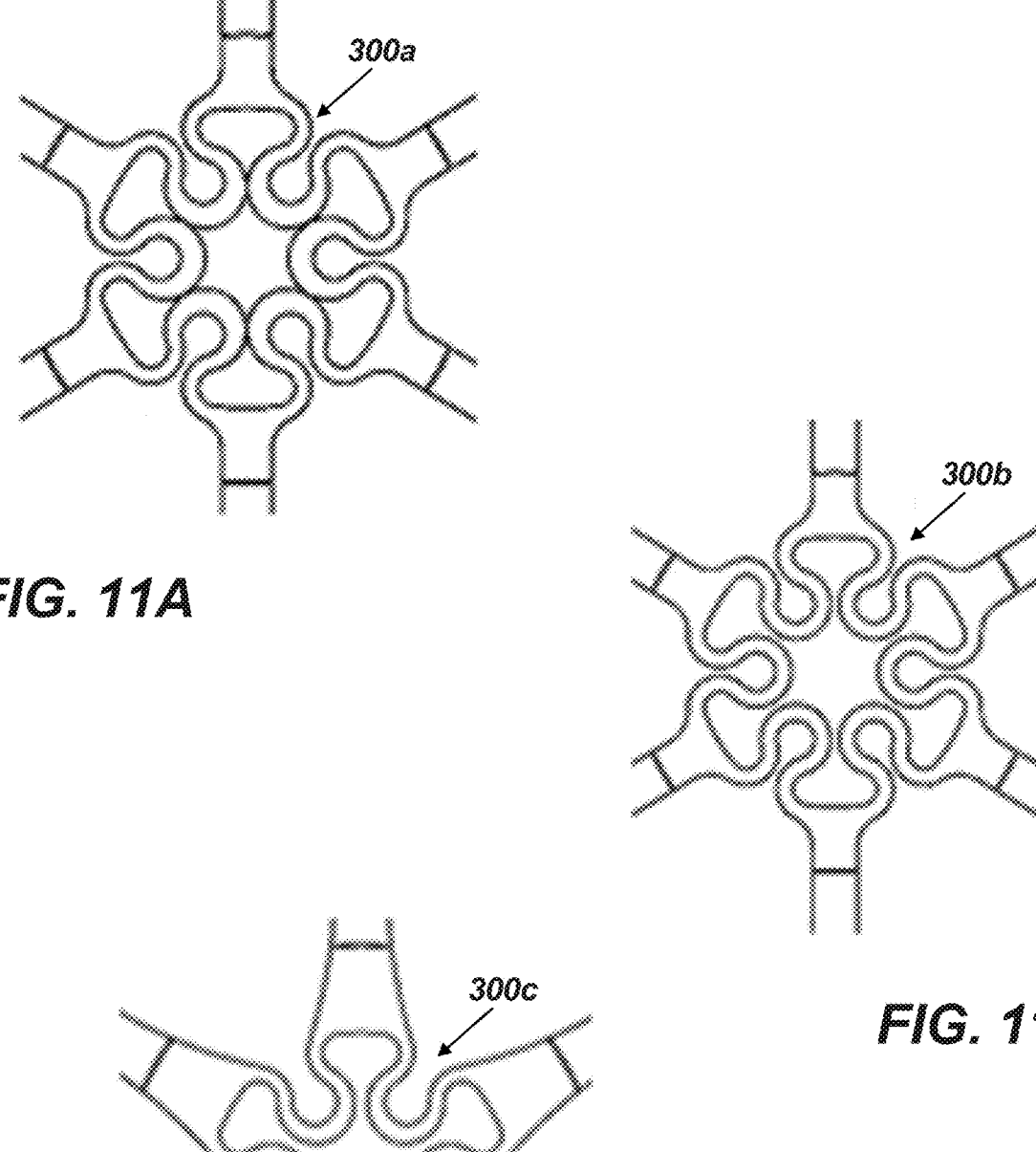
FIGS. 11A, 11B, and 11C illustrate distal end views of the cloverleaf structures with the dimensions illustrated in FIG. 10 varied.

FIGS. 11A, 11B, and 11C illustrate distal end views of example cloverleaf structures 300a, 300b, 300c with the three radii R1, R2, R3, the height H1, and the width T2 illustrated in FIG. 10 varied. The radius R1 of the first open area is set equal to the radius R3 of the third open area in these examples. The three structures 300a, 300b, 300c represent possible cloverleaf designs suitable for medical probe 22 with a range of lateral stiffness and a range of peak stress observed during retraction of the basket assembly 38 into a sheath or intermediate catheter.

Figure 12:
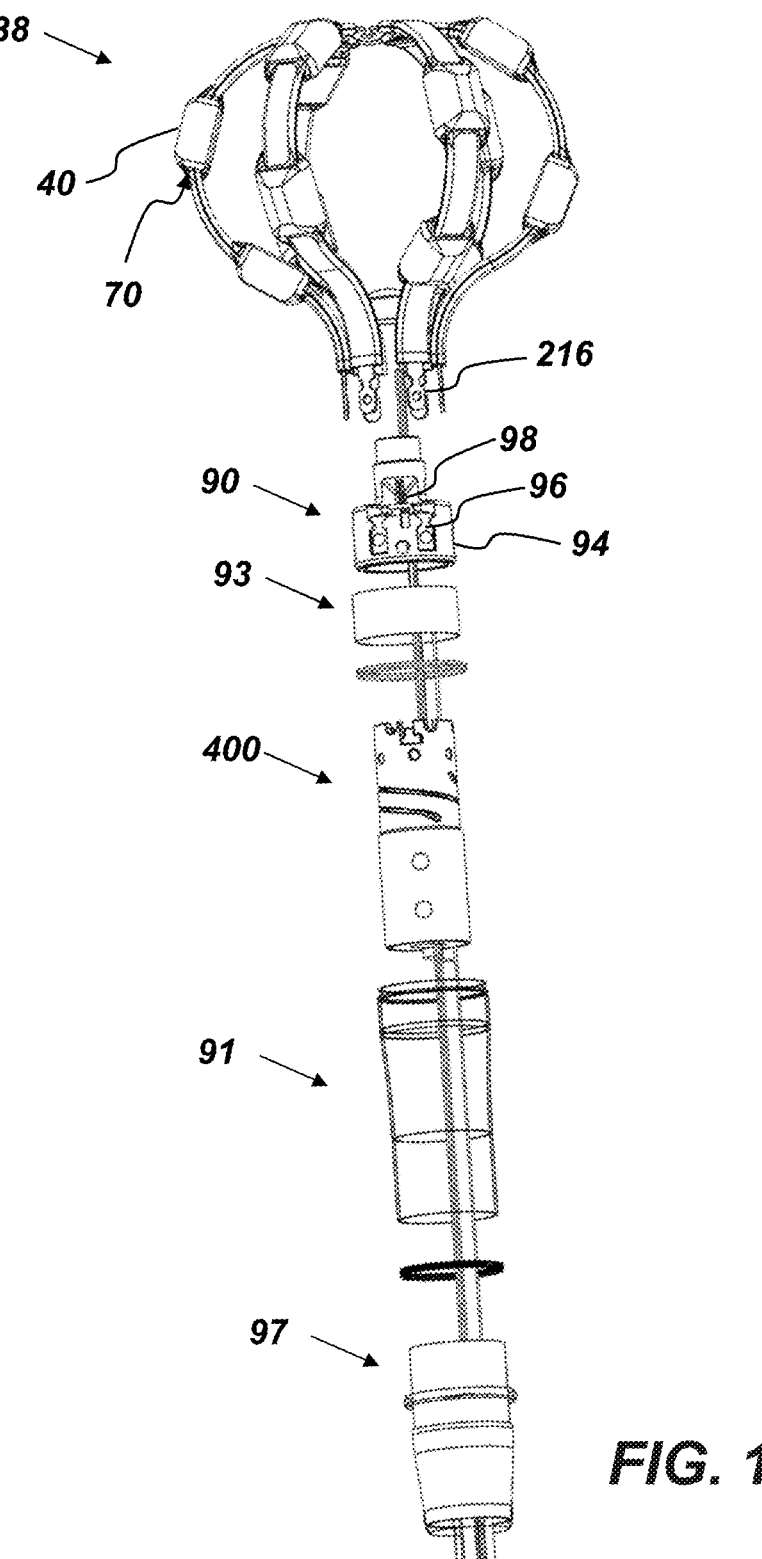
FIG. 12 illustrates an exploded view of the medical probe.

FIG. 12 illustrates an exploded view of the medical probe 22. Spines 214 can be attached to the spine retention hub 90 to form the basket assembly 38. A spine retention sleeve 93 can be disposed over the spine retention hub 90 to help secure the spines 214 in place. The contact force sensor assembly 400 can be coupled to the spine retention hub 90. The contact force sensor assembly 400 can be disposed in a contact force sensor assembly sleeve 91. The contact force sensor assembly sleeve 91 can be coupled to a proximal coupler 97 that can be coupled to the tubular shaft 84. When fully assembled, the basket assembly 38 can be attached to the tubular shaft 84 with the components just described to enable a medical professional 34 to insert the medical probe 22 into the heart 26 of a patient 28.

The spine retention hub 90 can include a cylindrical member 94 including a plurality of relief slots 96, multiple irrigation openings 98, and at least one spine retention hub electrode 99 (illustrated in FIG. 2), or some combination thereof. Relief slots 96 can be disposed on the outer surface of cylindrical member 94 and configured to allow a portion of each spine 214, such as each spine attachment end 216, to be fitted into a respective relief slot 96 of retention hub 90.

Figure 13A:
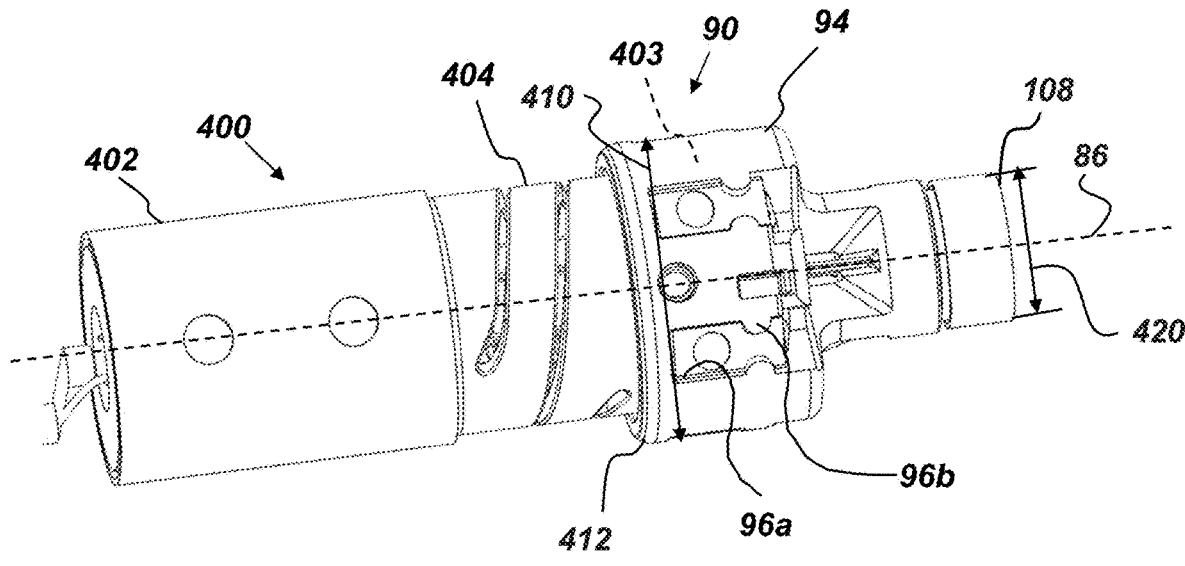
FIGS. 13A and 13B illustrate a contact force sensor assembly and spine retention hub of the medical probe.

FIG. 13A illustrates the spine retention hub 90. The relief slot 96 can include undercuts 96a running along the longitudinal axis to allow for insertion of spine attachment end 216. Relief slot 96 may be provided with tabs 96b that engage with complementary recess on spine retention end 216 to prevent twisting of the spine attachment end 216 of each spine 214 with respect to the retention hub 90. This configuration of the attachment ends 216 allow the multiple spines 214 at the proximal portion of the basket 38 to act as a single structural member with the retention hub 90. The spine retention hub 90 can also act as a coupler for a contact force sensor assembly 400. The attachment end 216 (FIG. 12) can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly 38 is deployed.

Figure 13B:
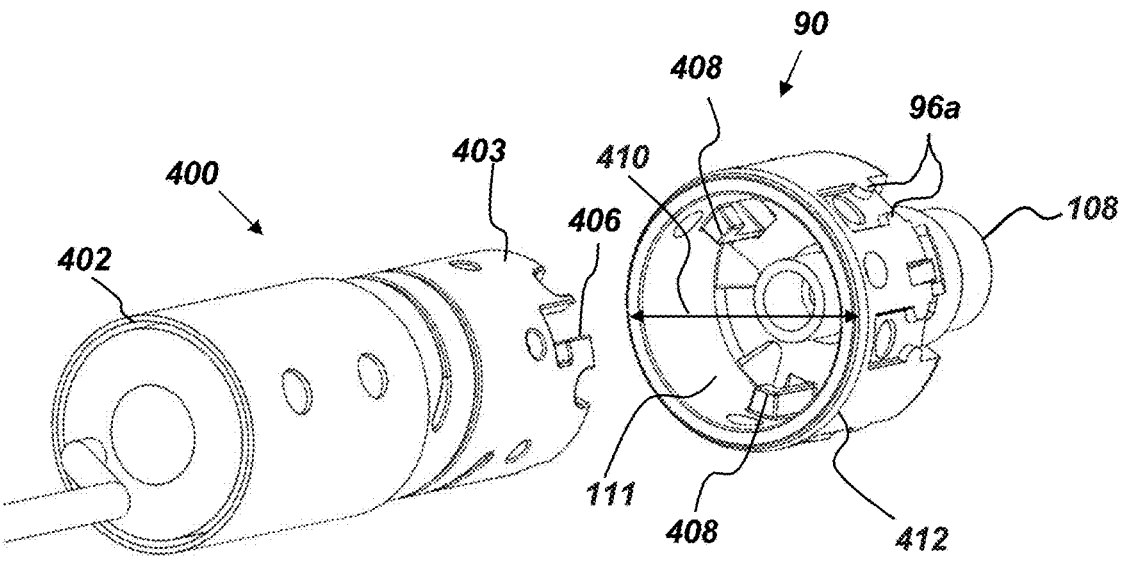

FIG. 13B is an illustration of the contact force sensor assembly 400 disconnected from the hub 90. The contact force sensor assembly 400 can include a proximal end 402 and a distal end 403. The distal end 403 is inserted into a cylindrical member 94 of the retention hub 90. The proximal end 402 can house a magnetic field sensor or sensors and the distal end can house a magnetic generator coil. The magnetic field generator coil can be configured to generate a magnetic field while the magnetic field sensor or sensors can be configured to detect the presence and magnitude of the magnetic field.

The contact force sensor assembly 400 can include a female connector 406 while the spine retention hub 90 can include a male connector 408. As will be appreciated, however, although shown and described for convenience as the contact force sensor assembly 400 having the female connector 406 and the spine retention hub 90 having the male connector 408, the two components can be switched around without departing from the scope of this disclosure. In other words, the contact force sensor assembly 400 can include the male connector 408 while the spine retention hub 90 can include the female connector 406 depending on the particular configuration. As will be appreciated, the contact force sensor assembly 400 can include a plurality of female connectors 406 while the spine retention hub 90 can include a plurality of male connectors 408. Alternatively, the contact force sensor assembly 400 can include both a female connector 406 and a male connector 408 while the spine retention hub can include a complimentary female connector 406 and a complimentary male connector 408.

The female connector 406 and the male connector 408 can form a bayonet mount configuration in which the male connector 408 can interlock with the female connector to couple the contact force sensor assembly 400 to the spine retention hub 90. Stated otherwise, the female connector 406 can comprise a slot forming a generally "L" shape and the male connector 408 can comprise a protrusion forming a generally complimentary "L" shape. In other words, the female connector 406 can include a slot having a first slot portion extending generally longitudinally into the contact force sensor assembly 400 from a distal end 403 of the contact force sensor assembly 400 and a second slot portion extending generally transversely from an end of the first slot portion. Similarly, the male connector 408 can include a protrusion having a first protrusion portion extending generally longitudinally away from the spine retention hub 90 and a second protrusion portion extending generally transversely from an end of the first protrusion portion.

The irrigation hub 90 can include a cylindrical member 94 extending along a longitudinal axis 86. The cylindrical member 94 can have a first outer diameter 410 at a proximal end 412 of the cylindrical member 94. The cylindrical member 94 can have a recess extending inwardly along the longitudinal axis 86 forming an interior portion 111. A distal end 108 having a second outer diameter 420 being less than the first outer diameter 410.

The contact force sensor assembly 400 can further include a deflection portion 404 disposed between the proximal end 402 and the distal end 403. The deflection portion 404 can be configured to deflect when a force is applied to the contact force sensor assembly 400. In other words, the deflection portion 404 can be configured to permit the proximal end 402 and the distal end 403 of the contact force sensor assembly 400 to move closer to each other when a force is applied to the contact force sensor assembly 400. In one example, the deflection portion 404 can include a helical spring formed into a body of the contact force sensor assembly 400. For example, helical cuts can be made in the body of the contact force sensor assembly 400 to form a helical spring. In this way, the body of the contact force sensor assembly 400 can itself form a spring without the need for additional components. In other examples, a spring can be assembled between the proximal end 402 and the distal end 403 to form the contact force sensor assembly 400. The contact force sensor assembly 400 can be disposed inside tube 84 (FIG. 2) and proximally in relation to the basket assembly 38 (FIG. 12) and as close as possible to the basket assembly 38 so that contact with cardiac tissue by the spines 214 can be transmitted to the contact force sensor assembly 400.

As will be appreciated, when the proximal end 402 is moved closer to the distal end 403 when a force is applied to the contact force sensor assembly 400, the magnetic field sensor housed in the proximal end 402 can detect a change in the magnitude of the force of the magnetic field generated by the magnetic field generator coil housed in the distal end 403. Because the spring constant K of the deflection portion 404 can be predetermined and the distance between the magnetic field generator coil and the magnetic field sensor can be detected, the force applied to the medical probe 22 can be determined (e.g., by using Hooke's law, or the equation F=d*K). Furthermore, the contact force sensor assembly 400 can receive electrical signals from, and provides electrical signals to, console 24, to process received signals and determine forces, e.g., sub-gram forces, exerted on the basket assembly 38.

Figure 14A:
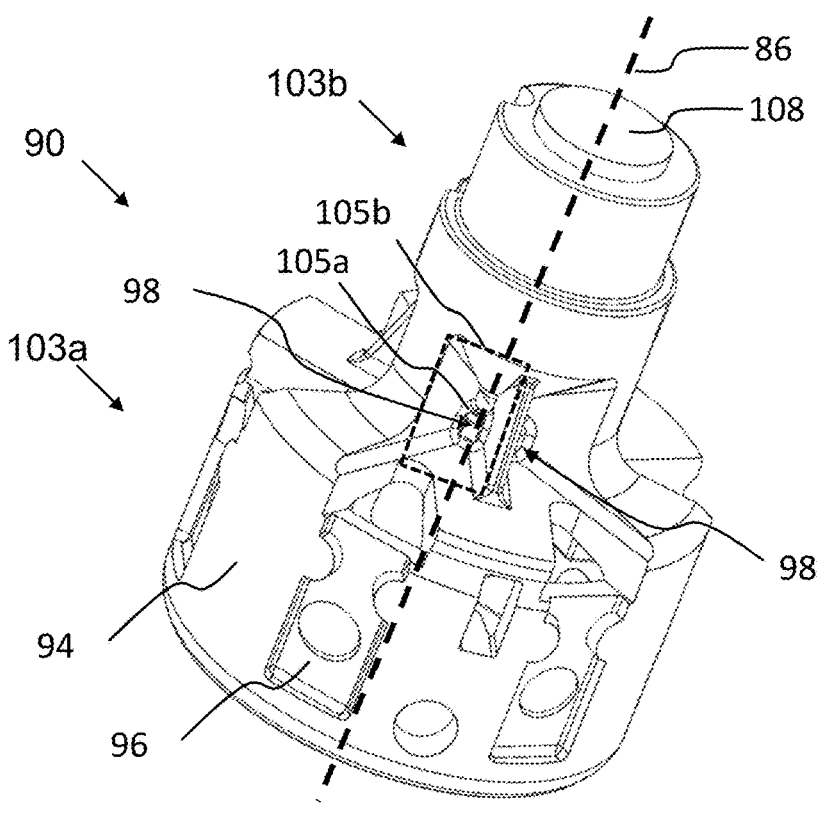
FIG. 14A is a schematic pictorial illustration showing a top perspective view of an irrigation hub, in accordance with the disclosed technology.
Figure 14B:
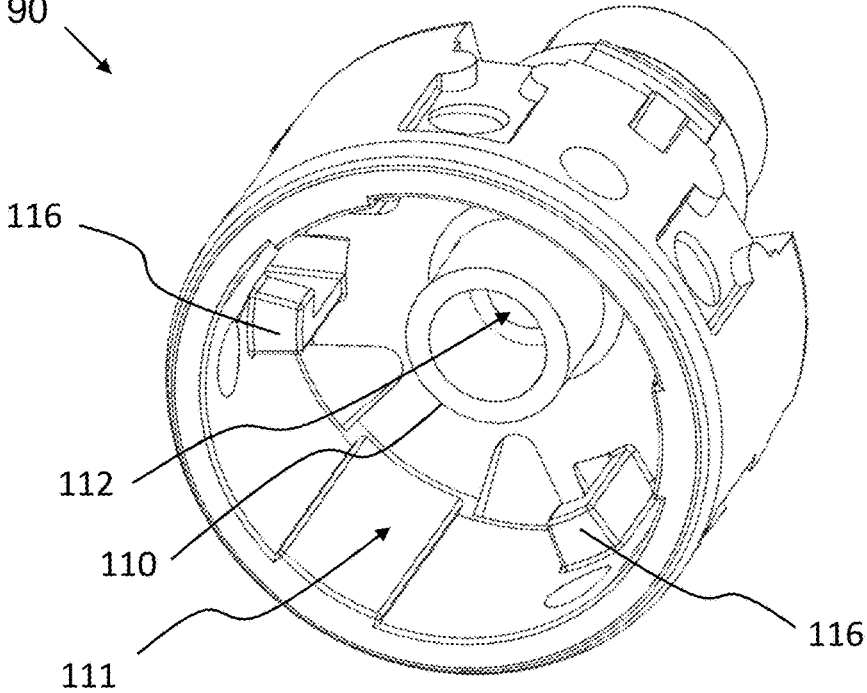
FIG. 14B is a schematic pictorial illustration showing a bottom perspective view of an irrigation hub, in accordance with the disclosed technology.

FIG. 14A is a schematic pictorial illustration showing a top perspective view of an irrigation hub 90 while FIG. 14B is a schematic pictorial illustration showing a bottom perspective view of an irrigation hub 90, in accordance with the disclosed technology. The irrigation hub 90 can additionally, or alternatively be configured to retain proximal spine ends similar to spine retention hub 90 illustrated in FIG. 2A. The irrigation hub 90 can be configured to deliver a fluid to the electrodes 40 of the medical probe 22. As shown in FIG. 14A, the irrigation hub 90 can include a cylindrical member 94 comprising a proximal end 103a and a distal end 103b. As shown, the proximal end 103a can have an outer diameter that is greater than an outer diameter of the distal end 103b.

The irrigation hub 90 can include a plurality of irrigation openings 98 that can be configured to permit fluid to flow therethrough and to help direct the fluid outwardly from the irrigation hub 90. The irrigation openings 98 can be dispersed radially around the distal end 103b and be generally transverse to the longitudinal axis 86. The irrigation openings 98 can each form an aperture having an inlet area 105a that is smaller than an outlet area 105b such that the fluid is permitted to disperse outwardly when directed out of the irrigation openings 98. In other words, as fluid flows through the irrigation hub 90 and out of the irrigation openings 98, the inlet area 105a through which the fluid first flows through the irrigation openings will be smaller than the outlet area 105b through which the fluid flows just prior to leaving the irrigation hub 90. In this way, the irrigation hub 90 can help to guide or direct the irrigation fluid toward the electrodes 40 or at least outwardly from the irrigation hub 90.

The irrigation hub 90 can further include a plurality of relief lands 96 that can be configured to receive and help retain the spines 22. As shown in FIG. 2A, the spines 214 can each include a spine attachment end 216 that can be configured to be at least partially inserted into the relief lands 96 such that the spines 214 can be secured in place with assembled with the irrigation hub 90.

The irrigation hub 90 can further include a sensor mount 108 that can be disposed at the distal end 103b of the cylindrical member 94. The sensor mount 108 can be configured to receive and support a sensor 608 (FIG. 16) of the medical probe 22. In some examples, the sensor 608 can be a reference electrode configured to detect far field signals that can be used in processing and filtering signals detected by the electrodes 40 when, for example, the electrodes 40 are used for mapping of electrical signals dispersed through a tissue. In other examples, the sensor can be or include one or more magnetic position sensors that can be used to detect magnetic fields output by one or more magnetic field generators to determine a position and/or orientation of the basket catheter 22.

Figure 17:
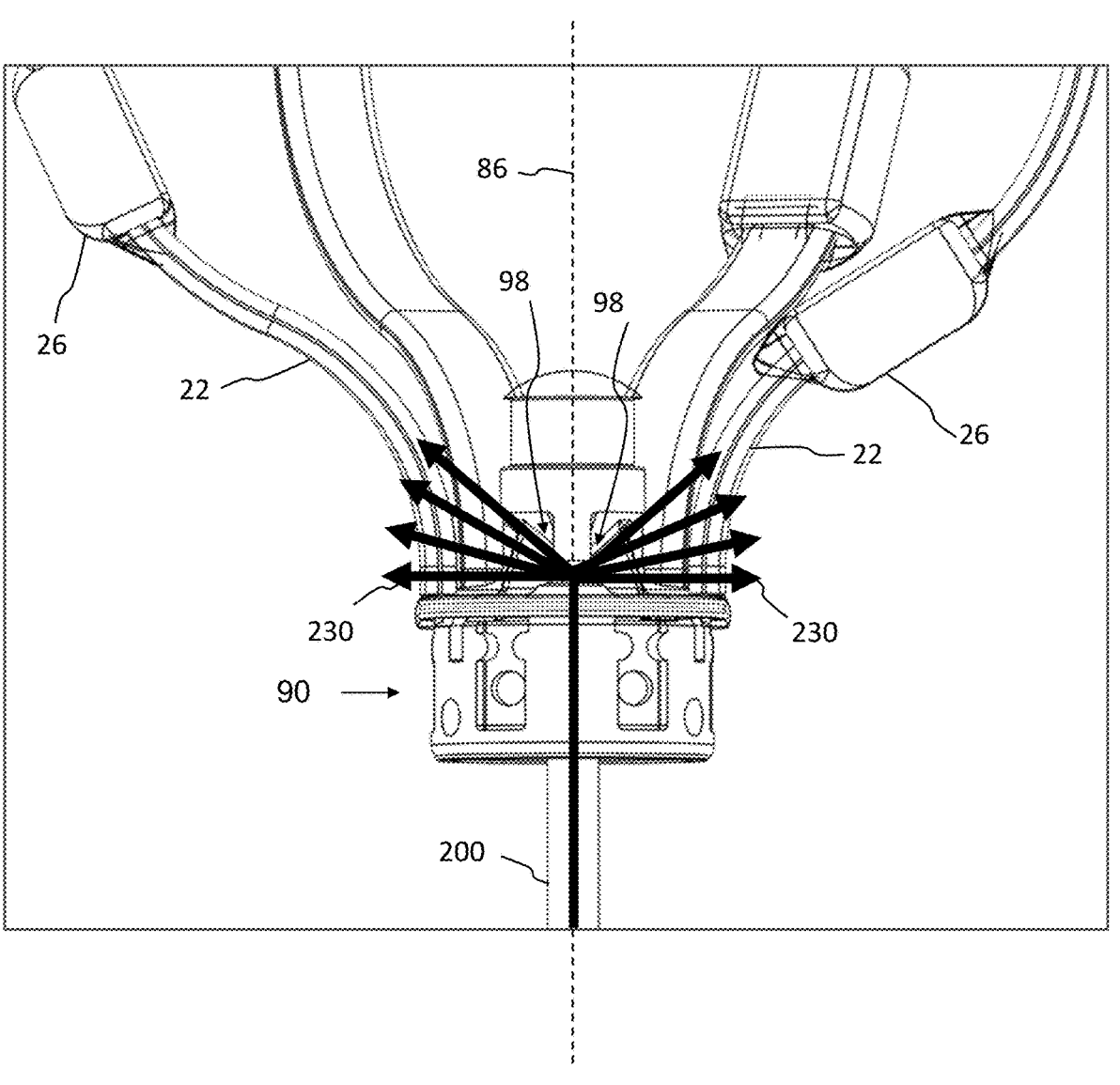
FIG. 17 is a schematic pictorial illustration showing flow of a fluid through an irrigation hub, in accordance with an embodiment of the present invention.

As shown in FIG. 14B, the proximal end 103a of the cylindrical member 94 can include a recess extending inwardly along the longitudinal axis 86 and forming an interior portion 111. The irrigation hub 90 can further include an irrigation coupler 110 that can be configured to receive, or otherwise be connected to, an irrigation supply tube 200 (as shown in FIG. 17). The cylindrical member 94 can further include an irrigation inlet chamber 112 that can be disposed distal the irrigation coupler 110 and proximal the interior portion 111. The irrigation inlet chamber 112 can be configured to receive fluid from the irrigation supply tube 200. The irrigation supply tube 200 can fluidly separate the fluid from the interior portion 111, the combination sensor 608, the tubular shaft 84 and other components of the medical probe. In other words, the fluid can be delivered to the irrigation inlet chamber 112 via the irrigation supply tube 200 without the fluid coming into contact with other interior components of the medical probe. The irrigation inlet chamber 112 can be sized to receive a sufficient amount of fluid from the irrigation supply tube 200 such that the flow of fluid is generally not impeded. In some examples, the irrigation inlet chamber 112 can have an inner diameter that is equal to the inner diameter of the irrigation supply tube 200. The irrigation inlet chamber 112 can be fluidly connected to the plurality of irrigation openings 98 such that the fluid can flow through the irrigation inlet chamber 112 and be directed out of the plurality of irrigation openings 98. The irrigation openings 98 can be disposed generally traverse to the longitudinal axis 86 from a distal portion of the irrigation inlet chamber 112.

The irrigation hub 90 can further include a plurality of attachment mechanisms 116 that can be configured for attaching the irrigation hub 90 to the combination sensor 608 and/or the tubular shaft 84. The attachment mechanisms 116 can be, for example and not limited to, bayonet mounts, snap connectors, a threaded fitting, or other suitable types of attachment mechanisms 116 for the particular application.

FIGS. 15A-15C illustrate various views of the irrigation hub 90. In particular, FIG. 15A illustrates a side view, FIG. 15B illustrates a top view, and FIG. 15C illustrates a bottom view of the irrigation hub 90, in accordance with the disclosed technology. Each of the reference numerals shown in FIGS. 15A-15C correspond to the various components and/or features described herein.

Figure 16:
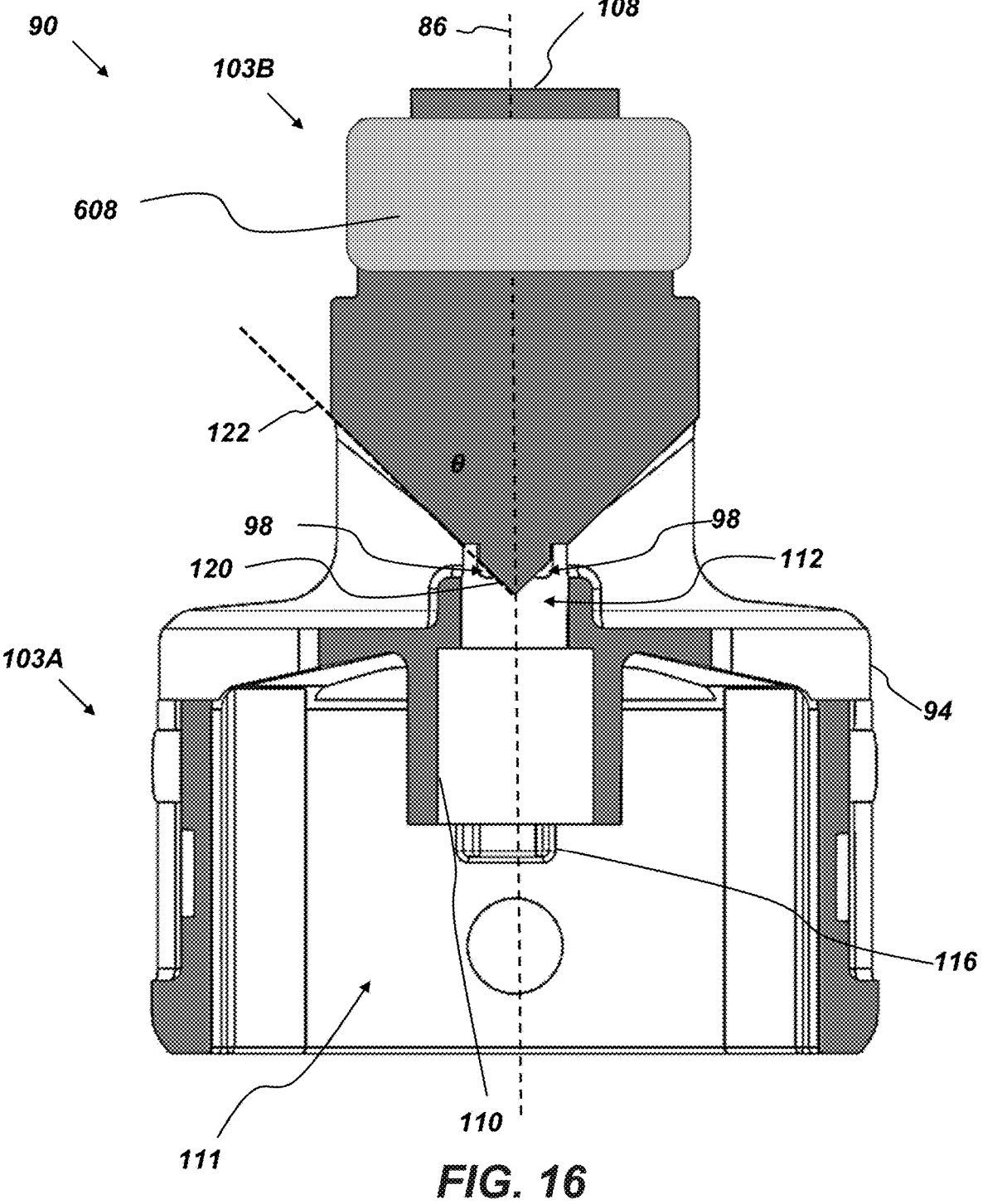
FIG. 16 is a schematic pictorial illustration showing a sectional view of an irrigation hub, in accordance with the disclosed technology.

FIG. 16 shows a sectional view of the irrigation hub 90, in accordance with the disclosed technology. As shown in FIG. 16, the irrigation hub 90 can include a flow diverter 120 disposed at a distal end of the irrigation inlet chamber 112 and extends inwardly into the irrigation inlet chamber 112.

By extending inwardly into the irrigation inlet chamber 112, the flow diverter 120 can block fluid flow and redirect fluid flow out of the irrigation openings in a direction generally traverse relative to the longitudinal axis 86, or at an angle to the longitudinal axis 86. The flow diverter 120, in some examples, can be a conical member that has an outer surface that extends at an angle θ away from the longitudinal axis 86. The angle θ can be a predetermined angle sufficient to redirect the fluid received from the irrigation supply tube 200 out the plurality of irrigation openings 98 such that the fluid is directed generally transverse to the longitudinal axis 86. In some examples, the angle θ can direct the fluid toward the electrodes 40. As non-limiting examples, the angle θ can be approximately 15°, 20°, 25°, 30°, 35°, 40°, 45°, 60°, 75°, 85°, or any other suitable angle for the particular application. Although described as a conical member, the flow diverter can comprise other shapes having generally planar sides, generally curves sides, or other configurations in which the fluid can be directed by the flow diverter 120 outwardly through the plurality of irrigation openings 98.

As will be appreciated, the irrigation openings 98 can extend outwardly from the irrigation inlet chamber 112 through the irrigation hub 90. As described previously, the irrigation openings 98 can include an inlet area 105a that is smaller than an outlet area 105b. The inlet area 105a can be near the irrigation inlet chamber 112 and the outlet area 105b can be disposed a distance away from the irrigation inlet chamber 112. A surface 122 of the irrigation openings 98 can extend between the inlet are 105a and the outlet are 105b. The surface 122 can be configured such that the surface is disposed at the angle θ or an angle that is substantially similar to the angle θ such that the fluid can be directed outwardly through the irrigation openings 98 without generating significant turbulence.

FIG. 16 further shows a sensor 608 attached to the sensor mount 108. As described supra, the sensor can be a magnetic position sensor, a reference electrode, or any other sensor for the particular configuration. Although the sensor 608 is shown as being disposed around or through the sensor mount 108, the sensor 608 can also be disposed at the very distal end of the sensor mount 108. In other examples, the sensor mount 108 can be configured to receive and support multiple sensors (e.g., a first sensor disposed around the sensor mount 108 and a second sensor disposed at the distal end of the sensor mount 108).

FIG. 17 illustrates a flow path 230 of a fluid through an irrigation hub 90, in accordance with an embodiment of the present invention. As shown in FIG. 17, the irrigation fluid can have a flow path 230 that extends through the irrigation supply tube 200 and is redirected by the irrigation hub 90 outwardly. In some examples, the irrigation hub 90 can redirect the fluid generally transverse to the longitudinal axis 86. In other examples, the irrigation hub 90 can redirect the fluid at other angles as described herein to obtain the desired cooling effect at the electrodes.

Figure 18A:
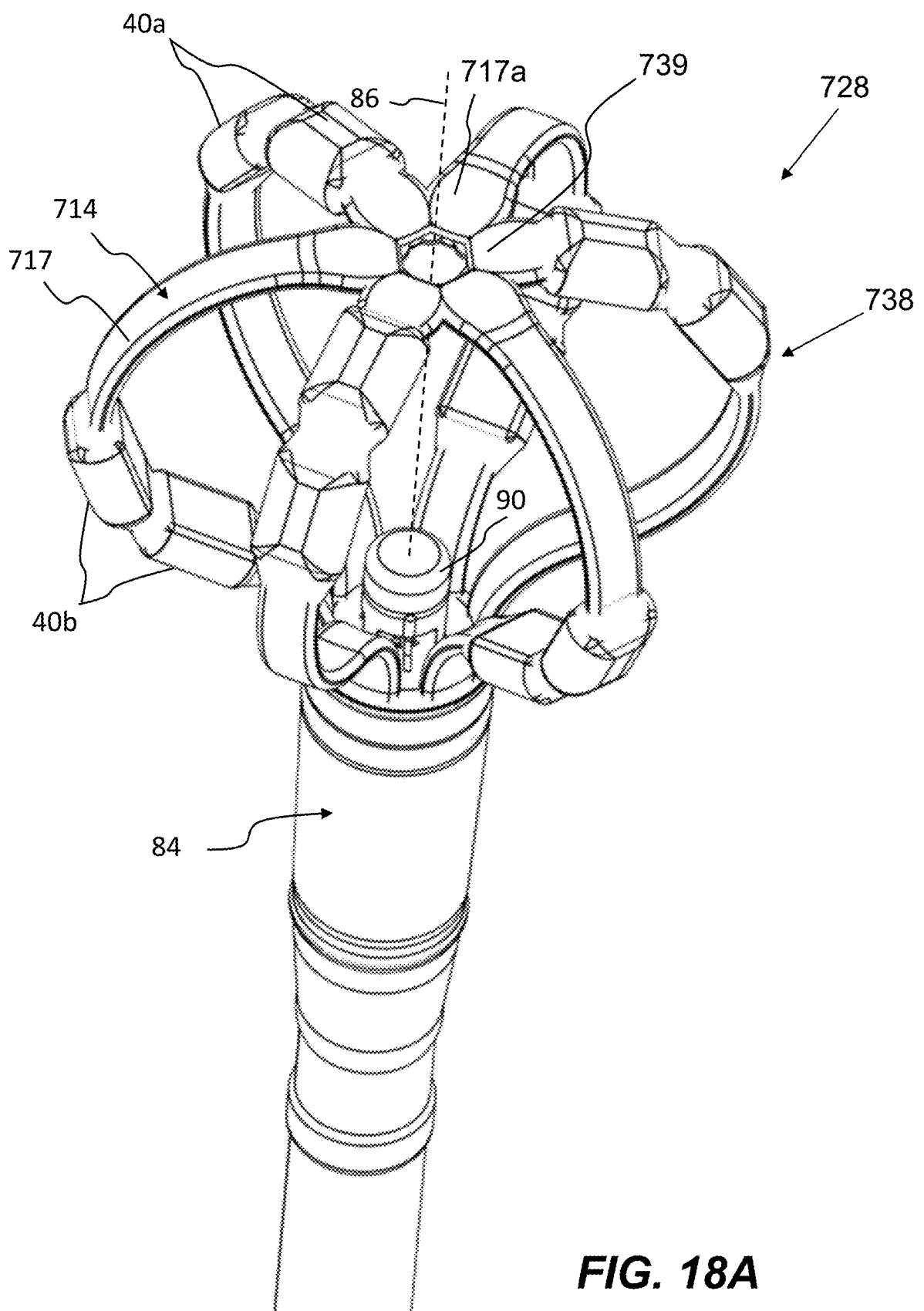
FIG. 18A is a schematic pictorial illustration showing a perspective view of another example medical probe with electrodes in an expanded form, in accordance with another example of the disclosed technology.
Figure 18B:
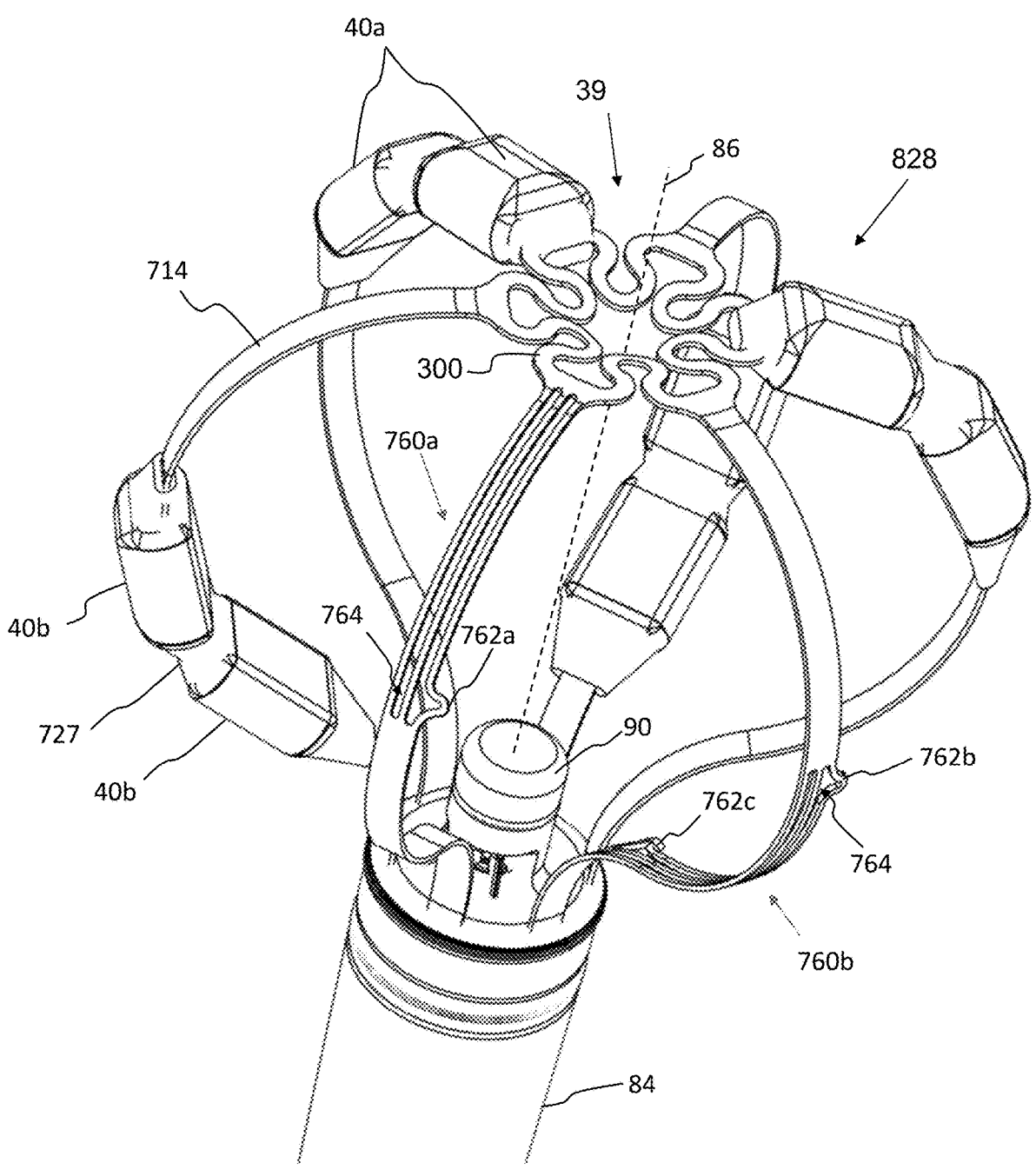
FIG. 18B is a schematic pictorial illustration showing a perspective view of the medical probe of 8A showing the spines, in accordance with the disclosed technology

FIGS. 18A and 18B illustrate another example basket catheter 728 with a basket assembly 738 having a plurality of electrodes 40a, 40b disposed on spines 714 and a hub 90 that can function similarly to the hub 90 illustrated elsewhere herein. As shown in FIG. 18A, the electrodes 40a, 40b can be disposed in alternating groupings of distal electrodes 40a and proximal electrodes 40b on adjacent spines 714. For example, and as shown in FIGS. 18A and 18B, two electrodes 40a, 40b can be disposed on the spines 714 close to each other with no additional electrodes 40a, 40b disposed on the same spine 714. On a first spine 714, the two electrodes 40b can be disposed together near the proximal end of the spine 714 while on a second, adjacent spine 714 two electrodes 40a can be disposed together near the distal end of the adjacent spines 714. In this way, the electrodes 40a, 40b can be offset around the circumference of the basket catheter 728 such that the basket assembly 738 is better able to collapse when retracted into a sheath. When the basket assembly 738 is collapsed, the distal electrodes 40a are positioned entirely in a distal direction from the proximal electrodes 40b with a gap along the longitudinal axis 86 between the proximal electrodes 40b and the distal electrode 40a.

With the configuration of electrodes 40a, 40b disposed on the spines 714 as shown in FIGS. 18A and 18B, the system 10 (FIG. 1) can be configured to output bipolar high-voltage DC pulses as may be used to effect irreversible electroporation (IRE) between the two adjacent electrodes 40a, 40b on a given spine 714, electrically connect the two adjacent electrodes 40a, 40b on a given spine 714 and output bipolar high-voltage DC pulses between one or more electrodes 40a, 40b on another one of the spines 714 of the basket assembly 738, and/or output monopolar high-voltage DC pulses between one or more of the electrodes 40a, 40b and the one or more electrode patches 44 (FIG. 1) disposed on the skin of a patient 28. The two electrodes 40a, 40b on a given spine 714 can include an insulative material 727 disposed between the two electrodes 40a, 40b, thereby electrically isolating the two electrodes 40a, 40b in an electrode pair from each other.

The spines 714 can be covered with an insulative liner or jacket 717 that can be disposed between the electrodes 40a, 40b and the frame of the spines 714. The insulative liner 717 can electrically isolate the electrodes 40a, 40b from the frame of the spines 714 to prevent arcing or shorting to the frame of the spines 714. The insulative liner 717 can extend from the hub 90 to the distal end 39 of the basket assembly 738.

FIG. 18B is an illustration of the basket assembly 738 with the insulative liners 717, a pair of distal electrodes 40a, and a pair of proximal electrodes 40b, and other spine elements removed, for the sake of illustration, so that the frame of the basket assembly 738 is visible. The spines 714 extend from the hub 90 and are joined together approximate a distal end 39 of the basket assembly 738 by a cloverleaf structure 300. The cloverleaf structure 300 can be configured similar to as disclosed in greater detail elsewhere herein, or a variation thereof. The insulative liner 717 can include flared ends 717a (FIG. 18A) that extend over a majority of the cloverleaf structure 300 (FIG. 18B) and may provide an atraumatic distal surface at the distal end 39 of the basket assembly 738. In this way, the insulative liner, or jacket 717 may prevent the frame of the basket assembly 738 from causing injury to tissue.

As illustrated in FIG. 18B, the spines 714 can further include an electrode retention region 760a, 760b that is configured to prevent an electrode 40a, 40b from sliding proximally or distally along the spine 714. Adjacent spines 714 can have spine retention regions 760a. 760b alternating between a proximal position and a distal position along the spine 714. That is, a first spine 714 can have an electrode retention region 760b disposed near a proximal end of the spine 714 and an adjacent spine 714 can have an electrode retention region 760a disposed near a distal end of the spine 714.

Each electrode retention region 760a, 760b can include one or more cutouts 764 that can permit the spine 714 to be bent or pinched inwardly. The plurality of spines 714 include a first spine having a distal electrode retention region 760a and a second spine having a proximal electrode retention region 760*b*. The first spine 714 has a single cross-section extending from a proximal portion of the first spine to approximately a midpoint of the first spine and thereafter dividing into at least two discrete cross sections (over the electrode retention region 760*a*) to the distal spine portion of the first spine (at the cloverleaf structure 300). The second spine 714 has at least two discrete cross sections extending from a proximal portion of the second spine (over the electrode retention region 760*b*) to approximately a midpoint of the second spine and thereafter combining into a single cross section extending to the distal spine portion of the second spine.

Each electrode retention region 760*a*, 760*b* can further include one or more retention members 762*a-c* that protrude outwardly and can be configured to prevent the electrode 40*a*, 40*b* from sliding proximally or distally along the spine 714. During manufacture, proximal ends of the frame of the basket assembly 738 are inserted into lumens of the electrodes 40*a*, 40*b*, and the electrodes 40*a*, 40*b* are slid distally along the spines 714 to their respective final position. The cutouts 764 permit the electrodes 40*a*, 40*b* to slide over a retention members 762*a-c*. Because of the one or more cutouts 764 in the spines 714, the retention members 762*a-c* can be configured to move inwardly when the spine 714 is pinched inwardly to permit an electrode 40*a*, 40*b* to slide over the retention member 762*a-c*. Once the electrode 40*a*, 40*b* is slid past the retention member 762, the retention member 762 can resiliently bend back to its previous position, thereby preventing the electrode 40*a*, 40*b* from sliding proximally or distally along the spine 714.

The proximal electrode retention region 760*b* includes a proximal retention member 762*c* and a distal retention member 762*b*. The proximal electrode retention region 760*b* need not be configured to permit the proximal electrodes 40*b* to pass over the distal retention member 762*b*. The distal electrode retention region 760*a* utilizes the cloverleaf structure 300 to prevent the distal electrodes 40*a* from moving distally once the distal electrodes 40*a* are in their respective final position.

Although the basket catheter 728 is shown as having two electrodes 40*a*, 40*b* disposed near each other on a given spine 714 and having alternating groupings of electrodes 40*a*, 40*b* on adjacent spines 714, the disclosed technology can include other configurations of electrodes and spines not shown. For example, the disclosed technology can include groupings of three or more electrodes and/or multiple groupings of electrodes disposed on spines, and may further include differing numbers of spines. Thus, the disclosed technology is not limited to the particular configuration of electrodes and spines shown and described herein.

The following clauses list non-limiting embodiments of the disclosure:

Clause 1. A medical probe, comprising: an expandable basket assembly configured to be coupled to a distal end of the tubular shaft, the basket assembly comprising: a plurality of spines extending along the longitudinal axis from a proximal central proximal spine portion to a distal spine portion, the distal spine portion defining a cloverleaf structure disposed radially around the longitudinal axis, the cloverleaf structure defining a central cutout with a central area disposed about the longitudinal axis, the cloverleaf structure comprising a sinusoidal-like member extending from one spine to an adjacent spine in a direction around the longitudinal axis, the sinusoidal-like member meanders around: (a) a first virtual circle having a first radius, the first virtual circle having its center located at a first distance to the longitudinal axis, (b) a second virtual circle having a second radius, the second virtual circle having its center located at a second distance smaller than the first distance to the longitudinal axis, and (c) a third virtual circle having a third radius approximately equal to the first radius, the third virtual circle having its center located at a third distance approximately equal to the first distance to the longitudinal axis, the cloverleaf structure further defining a height measured from a point on a perimeter of the second virtual circle to a neck directly away from the longitudinal axis in relation to the second virtual circle and between an adjacent first virtual circle and second virtual circle, the first radius, second radius, third radius, and height being configured to provide a lateral stiffness of the expandable basket assembly within a predetermined range.

Clause 2. The medical probe according to clause 1, the first radius, second radius, third radius, and height being configured to provide a maximum peak stress during retraction of the expandable basket assembly into an intermediate catheter such that the maximum peak stress is less than a predetermined threshold.

Clause 3. The medical probe according to clause 1 or 2, wherein the first radius measures about 33% of the height, wherein the second radius measures about 39% of the height, wherein the third radius measures about 33% of the height, and wherein the width measures about 25% of the height.

Clause 4. The medical probe according to any one of clauses 1-3, wherein the first radius measures between 31% and 35% of the height, wherein the second radius measures between 37% and 41% of the height, wherein the third radius measures between 31% and 35% of the height, and wherein the width measures between 23% and 27% of the height.

Clause 5. The medical probe according to any one of clauses 1-4, wherein the central area comprises approximately 0.8 mm-squared area, a fourth virtual circle encircling the sinusoidal-like member comprises an area approximately 14 times greater than the central area and each of the first and third virtual circle is located at a first distance from the central axis while the second virtual circle is located at a second distance of approximately ½ that of the first distance.

Clause 6. The medical probe according to clause 5, in which the sinusoidal-like member is tangential to the central circle.

Clause 7. The medical probe according to any one of clauses 1-6, wherein the expandable basket assembly comprises a coating covering the sinusoidal-like member and a central cutout circumscribed by the sinusoidal-like member.

Clause 8. The medical probe according to any one of clauses 1-6, wherein the expandable basket assembly comprises a coating covering a majority of the sinusoidal-like member and comprises an opening at the longitudinal axis.

Clause 9. The medical probe according to any one of clauses 1-8, wherein a cross-sectional shape of each electrode comprises a substantially ovoid or trapezoidal shape.

Clause 10. The medical probe according to any one of clauses 1-9, wherein each of the spines includes at least one retention member extending generally transverse to the spine.

Clause 11. The medical probe according to clause 10, further comprising: a plurality of electrodes, wherein each electrode of the plurality of electrodes comprises a body defining a hollow portion extending through the body of the electrode so that a spine can be inserted into the hollow portion and retained by the at least one retention member.

Clause 12. The medical probe according to clause 10 or 11, in which the at least one retention member comprises a bow shaped member.

Clause 13. The medical probe according to any one of clauses 10-12, in which the at least one retention member comprises two bow shaped members disposed in opposite direction and transverse to a longer length of each spine.

Clause 14. The medical probe according to any one of clauses 10-13, in which the at least one retention member comprises first and second sets of retention members spaced apart along the spines, the first set includes two bow shaped members disposed in opposite direction and transverse to a longer length of each spine and the second set includes two bow shaped members disposed in opposite direction and transverse to a longer length of each spine so that each electrode is captured between the first and second sets of retention members.

Clause 15. The medical probe according to any one of clauses 1-14, wherein the plurality of spines extends from the proximal central spine portion in an equiangular pattern such that respective angles between respectively adjacent spines are approximately equal.

Clause 16. The medical probe according to any one of clauses 1-15, further comprising a plurality of electrically insulative jackets each disposed between a respective spine of the plurality of spines and a respective electrode, thereby electrically isolating the respective electrode from the respective spine.

Clause 17. The medical probe according to clause 16, wherein the sinusoidal-like member comprises an inner arc around the second virtual circle such that the inner arc is entirely positioned less than the second distance from the longitudinal axis, wherein the sinusoidal-like member comprises an outer portion around the first virtual circle and around the second virtual circle such that the outer portion is entirely positioned greater than the second distance from the longitudinal axis, and wherein a majority of the outer portion of the sinusoidal-like member is covered by a respective jacket of the electrically insulative jackets.

Clause 18. The medical probe according to clause 17, wherein at least a portion of the inner arc of the sinusoidal-like member is exposed to environment.

Clause 19. The medical probe according to clause 17 or 18, wherein a distal portion of each of the plurality of electrically insulative jackets tapers outward and inward, following a curvature of the outer portion of the sinusoidal-like member.

Clause 20. The medical probe according to any one of clauses 17-19, a distal portion of each of the plurality of electrically insulative jackets abuts the distal portion of an adjacent insulative jacket.

Clause 21. The medical probe according to any one of clauses 16-20, further comprising: two electrodes coupled to a respective spine for each spine of the plurality of spines.

Clause 22. The medical probe according to any one of clauses 16-21, further comprising: a wire disposed inside a respective jacket the plurality of electrically insulative jackets, wherein the wire is electrically connected to the respective electrode.

Clause 23. The medical probe according to any of clauses 1-22, wherein the plurality of spines comprise a material selected from a group consisting of nitinol, cobalt chromium, stainless steel, titanium, and combinations hereof.

Clause 24. The medical probe according to any of clauses 11-23, wherein each electrode comprises of a material selected from stainless steel, cobalt chromium, gold, platinum, palladium, and alloys or combinations hereof.

Clause 25. The medical probe according to any one of clauses 1-24, further comprising: a plurality of electrodes configured to deliver electrical pulses for irreversible electroporation, the pulses including a peak voltage of at least 900 volts (V).

Clause 26. The medical probe according to any one of clauses 1-25, wherein the plurality of spines is configured to form an approximately spherically-shaped basket assembly when in the expanded form.

Clause 27. The medical probe of according to any one of clauses 1-25, wherein the plurality of spines is configured form an approximately oblate-spheroid basket assembly when in the expanded form.

Clause 28. The medical probe according to any one of clauses 1-27, further comprising irrigation ports disposed in the proximal portion of the basket to deliver an irrigation fluid to the plurality of electrodes.

Clause 29. The medical probe according to any one of clauses 1-28, in which the central cutout approximates a central circle with a central area and wherein the cloverleaf structure is disposed within a fourth circle with its center on the longitudinal axis so that portions of the cloverleaf close to the center circle is spaced apart along the longitudinal axis with respect to portions of the cloverleaf close to the fourth circle thereby defining a concave cloverleaf structure.

Clause 30. The medical probe according to any one of clauses 1-29, in which the cloverleaf structure is concave with its center extending towards the proximal central spine portion of the basket to approximate a concave surface disposed about the longitudinal axis.

Clause 31. The medical probe according to any one of clauses 1-30, in which a reference electrode is disposed proximate the distal end of the tubular shaft.

Clause 32. The medical probe according to any one of clauses 1-31, in which a spine retention hub is coupled to the distal end of the tubular shaft to connect the spines to the retention hub.

Clause 33. The medical probe according to any one of clauses 1-32, in which a cylindrical projection is provided to locate the reference electrode on the projection.

Clause 34. The medical probe according to any one of clauses 1-33, in which the spine retention hub includes outlet ports to allow fluid delivered to the distal end tubular shaft to exit the outlet ports into a volume surrounded by the basket spines.

Clause 35. A method of constructing a medical probe, the method comprising: cutting a tubular frame including a plurality of spines extending along a longitudinal axis from a proximal spine portion to a distal spine portion, the distal spine portion defining a cloverleaf structure disposed radially around the longitudinal axis, the tubular frame being configured to move from a tubular shape to an expanded basket shape in which: the plurality of spines bow away from the longitudinal axis, the cloverleaf structure defines a central cutout with a central area disposed about the longitudinal axis, the cloverleaf structure comprises a sinusoidal-like member extending from one spine to an adjacent spine in a direction around the longitudinal axis, the sinusoidal-like member meanders around: (a) a first virtual circle having a first radius, the first virtual circle having its center located at a first distance to the longitudinal axis, (b) a second virtual circle having a second radius, the second virtual circle having its center located at a second distance smaller than the first distance to the longitudinal axis, and (c) a third virtual circle having a third radius approximately equal to the first radius, the third virtual circle having its center located at a third distance approximately equal to the first distance to the longitudinal axis, the cloverleaf structure further defining a height measured from a point on a perimeter of the second virtual circle to a neck directly away from the longitudinal axis in relation to the second virtual circle and between an adjacent first virtual circle and second virtual circle; and forming a basket assembly for the medical probe such that the tubular frame provide structure support for the basket assembly, and such that the first radius, second radius, third radius, and height are configured to provide a lateral stiffness of the expandable basket assembly within a predetermined range.

Clause 36. The method of clause 35, the first radius, second radius, third radius, and height being configured to provide a maximum peak stress during retraction of the expandable basket assembly into an intermediate catheter such that the maximum peak stress is less than a predetermined threshold.

Clause 37. The method of clause 35 or 36, wherein the first radius measures about 33% of the height, wherein the second radius measures about 39% of the height, wherein the third radius measures about 33% of the height, and wherein the width measures about 25% of the height.

Clause 38. The method of any one of clauses 35-37, wherein the first radius measures between 31% and 35% of the height, wherein the second radius measures between 37% and 41% of the height, wherein the third radius measures between 31% and 35% of the height, and wherein the width measures between 23% and 27% of the height.

Clause 39. The method of any one of clauses 35-38, further comprising: aligning the plurality of spines with a plurality of electrodes each having a lumen extending through the body of the electrode; inserting each spine of the plurality of spines into the lumen of an electrode of the plurality of electrodes; and retaining the plurality of electrodes on the plurality of spines.

Clause 40. The method of clause 39, wherein retaining the plurality of electrodes on the plurality of spines comprises retaining an electrode of the plurality of electrodes with at least one biasing member.

Clause 41. The method of clause 40, in which the at least one biasing member is disposed outside of the lumen of the electrode.

Clause 42. The method of clause 40 or 41, in which the at least one biasing member is disposed inside the lumen of the electrode.

Clause 43. The method according to any one of clauses 35-42, further comprising: positioning the spine of the expandable basket assembly through a lumen of an electrically insulative jacket of the plurality of electrically insulative jackets; positioning a wire through the lumen of the electrically insulative jacket; positioning an electrode of the plurality of electrodes over the electrically insulative jacket; and electrically connecting the wire to the electrode through an aperture in the electrically insulative jacket.

Clause 44. The method of clause 43, further comprising: covering a majority of the sinusoidal like member with the plurality of electrically insulative jackets.

Clause 45. The method of clause 44, a distal portion of each of the plurality of electrically insulative jackets abuts the distal portion of an adjacent insulative jacket.

Clause 46. The method of clause 44 or 45, further comprising: covering a majority of an outer portion of the sinusoidal-like member with the plurality of electrically insulative jackets such that the outer portion of the sinusoidal-like member meanders around the first virtual circle and around the second virtual circle, and such that the outer portion is entirely positioned greater than the second distance from the longitudinal axis.

Clause 47. The method of clause 46, wherein an inner arc of the sinusoidal-like member remains exposed to environment such that the inner arc meanders around the second virtual circle, and such that the inner arc is entirely positioned less than the second distance from the longitudinal axis.

Clause 48. The method of clause 46 or 47, wherein a distal portion of each of the plurality of electrically insulative jackets tapers outward and inward, following a curvature of the outer portion of the sinusoidal-like member.

Clause 49. The method of any one of clauses 35-48, wherein each respective spine of a plurality of spines comprises a first electrode and a second electrode thereon, the method further comprising: aligning each respective spine of the plurality of spines with the first electrode and the second electrode; inserting each respective spine of the plurality of spines into a lumen of the first electrode and a lumen of the second electrode; and fitting an end of each respective spine of the plurality of spines to the tubular shaft sized to traverse vasculature.

Clause 50. The method of any one of clauses 39-49, further comprising offsetting the electrodes between adjacent spines along the longitudinal axis.

Clause 51. The method of any of clauses 39-50, wherein the electrode body lumen is configured to receive the wire of the medical probe.

Clause 52. The method of any of clauses 39-51, wherein the wire is insulated from the spine.

Clause 53. The medical probe of clause 16, further comprising: two electrodes coupled to a respective spine for each spine of the plurality of spines, the plurality of spines comprising a first spine having a single cross-section extending from a proximal portion to approximately a midpoint of the first spine and thereafter dividing into at least two discrete cross sections to the distal portion of the first spine and a second spine having at least two discrete cross sections extending from a proximal portion to approximately a midpoint of the second spine and thereafter combining into a single cross section extending to the distal portion of the second spine.

Clause 54. The medical probe of clause 1, further comprising: an irrigation hub coupled to the tubular shaft, the irrigation hub comprising a cylindrical member extending along a longitudinal axis, the cylindrical member comprising: a proximal end having a first outer diameter and a recess extending inwardly along the longitudinal axis forming an interior portion; a distal end having a second outer diameter, the second outer diameter being less than the first outer diameter; an irrigation inlet chamber disposed proximate the interior portion and configured to receive fluid from an irrigation supply; a plurality of irrigation openings disposed generally transverse to the longitudinal axis from a distal portion of the irrigation inlet chamber; and a flow diverter extending into the distal portion of the irrigation inlet chamber to block fluid flow and redirect fluid flow out of the plurality of irrigation openings in a direction generally transverse relative to the longitudinal axis.

Clause 55. The medical probe according to clause 1, in which the cloverleaf structure is concave with its center extending towards the proximal central spine portion of the basket to approximate a concave surface disposed about the longitudinal axis further comprising: a contact force sensor assembly disposed at the distal end of the tubular shaft and configured to detect a force applied to the medical probe, the contact force sensor assembly comprising: a first bayonet mount portion that includes components of the contact force assembly; a spine retention hub comprising a plurality of slots to receive respective spine members of the expandable basket assembly; and, a second bayonet mount portion configured to couple the spine retention hub to the contact force sensor assembly by interlocking with the first bayonet mount portion.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A medical probe, comprising:
an expandable basket assembly configured to be coupled to a distal end of a tubular shaft, the basket assembly comprising:
a plurality of spines extending along a longitudinal axis from a proximal central proximal spine portion to a distal spine portion, the distal spine portion defining a cloverleaf structure disposed radially around the longitudinal axis, the cloverleaf structure defining a central cutout with a central area disposed about the longitudinal axis, the cloverleaf structure comprising a sinusoidal-like member extending from one spine to an adjacent spine in a direction around the longitudinal axis, the sinusoidal-like member meanders around:
(a) a first virtual circle having a first radius, the first virtual circle having its center located at a first distance to the longitudinal axis,
(b) a second virtual circle having a second radius, the second virtual circle having its center located at a second distance smaller than the first distance to the longitudinal axis, and
(c) a third virtual circle having a third radius approximately equal to the first radius, the third virtual circle having its center located at a third distance approximately equal to the first distance to the longitudinal axis,
the cloverleaf structure further defining a height measured from a point on a perimeter of the second virtual circle to a neck directly away from the longitudinal axis in relation to the second virtual circle and between an adjacent first virtual circle and second virtual circle,
the first radius, second radius, third radius, and height being configured to provide a lateral stiffness of the expandable basket assembly within a predetermined range,
wherein the first radius measures between 31% and 35% of the height,
wherein the second radius measures between 37% and 41% of the height,
wherein the third radius measures between 31% and 35% of the height, and
wherein a minimum width of the sinusoidal-like member measures between 23% and 27% of the height.

2. The medical probe according to claim 1, the first radius, second radius, third radius, and height being configured to provide a maximum peak stress during retraction of the expandable basket assembly into an intermediate catheter such that the maximum peak stress is less than a predetermined threshold.

3. The medical probe according to claim 1,
wherein the first radius measures about 33% of the height,
wherein the second radius measures about 39% of the height,
wherein the third radius measures about 33% of the height, and
wherein a minimum width of the sinusoidal-like member measures about 25% of the height.

4. The medical probe according to claim 1, wherein the central area comprises approximately 0.8 mm-squared area, a fourth virtual circle encircling the sinusoidal-like member comprises an area approximately 14 times greater than the central area and the second distance is approximately ½ that of the first distance.

5. The medical probe according to claim 4, in which the sinusoidal-like member is tangential to a central circle of the central area.

6. The medical probe according to claim 1, further comprising a plurality of electrically insulative jackets each disposed between a respective spine of the plurality of spines and a respective electrode, thereby electrically isolating the respective electrode from the respective spine.

7. The medical probe according to claim 6,
wherein the sinusoidal-like member comprises an inner arc around the second virtual circle such that the inner arc is entirely positioned less than the second distance from the longitudinal axis,
wherein the sinusoidal-like member comprises an outer portion around the first virtual circle and around the second virtual circle such that the outer portion is entirely positioned greater than the second distance from the longitudinal axis, and
wherein a majority of the outer portion of the sinusoidal-like member is covered by a respective jacket of the electrically insulative jackets.

8. The medical probe according to claim 7, wherein a distal portion of each of the plurality of electrically insulative jackets tapers outward and inward, following a curvature of the outer portion of the sinusoidal-like member.

9. The medical probe according to claim 7, a distal portion of each of the plurality of electrically insulative jackets abuts the distal portion of an adjacent insulative jacket.

10. The medical probe according to claim 6, further comprising:
two electrodes coupled to a respective spine for each spine of the plurality of spines, the plurality of spines comprising a first spine and a second spine, the first spine having a single cross-section extending from a proximal portion of the first spine to approximately a midpoint of the first spine and thereafter dividing into at least two discrete cross sections to the distal spine portion of the first spine, and the second spine having at least two discrete cross sections extending from a proximal portion of the second spine to approximately a midpoint of the second spine and thereafter combining into a single cross section extending to the distal spine portion of the second spine.

11. A medical probe, comprising:
an expandable basket assembly configured to be coupled to a distal end of a tubular shaft, the basket assembly comprising:
a plurality of spines extending along a longitudinal axis from a proximal central proximal spine portion to a distal spine portion, the distal spine portion defining a cloverleaf structure disposed radially around the longitudinal axis, the cloverleaf structure defining a central cutout with a central area disposed about the longitudinal axis, the cloverleaf structure comprising a sinusoidal-like member extending from one spine to an adjacent spine in a direction around the longitudinal axis, the sinusoidal-like member meanders around:

(a) a first virtual circle having a first radius, the first virtual circle having its center located at a first distance to the longitudinal axis, (b) a second virtual circle having a second radius, the second virtual circle having its center located at a second distance smaller than the first distance to the longitudinal axis, and (c) a third virtual circle having a third radius approximately equal to the first radius, the third virtual circle having its center located at a third distance approximately equal to the first distance to the longitudinal axis, the cloverleaf structure further defining a height measured from a point on a perimeter of the second virtual circle to a neck directly away from the longitudinal axis in relation to the second virtual circle and between an adjacent first virtual circle and second virtual circle, the first radius, second radius, third radius, and height being configured to provide a lateral stiffness of the expandable basket assembly within a predetermined range, wherein the central area comprises approximately 0.8 mm-squared area, a fourth virtual circle encircling the sinusoidal-like member comprises an area approximately 14 times greater than the central area and the second distance is approximately ½ that of the first distance.

12. The medical probe according to claim 11, the first radius, second radius, third radius, and height being configured to provide a maximum peak stress during retraction of the expandable basket assembly into an intermediate catheter such that the maximum peak stress is less than a predetermined threshold.

13. The medical probe according to claim 11, wherein the first radius measures about 33% of the height, wherein the second radius measures about 39% of the height, wherein the third radius measures about 33% of the height, and wherein a minimum width of the sinusoidal-like member measures about 25% of the height.

14. The medical probe according to claim 11, in which the sinusoidal-like member is tangential to a central circle of the central area.

15. The medical probe according to claim 11, further comprising a plurality of electrically insulative jackets each disposed between a respective spine of the plurality of spines and a respective electrode, thereby electrically isolating the respective electrode from the respective spine.

16. The medical probe according to claim 15, wherein the sinusoidal-like member comprises an inner arc around the second virtual circle such that the inner arc is entirely positioned less than the second distance from the longitudinal axis, wherein the sinusoidal-like member comprises an outer portion around the first virtual circle and around the second virtual circle such that the outer portion is entirely positioned greater than the second distance from the longitudinal axis, and wherein a majority of the outer portion of the sinusoidal-like member is covered by a respective jacket of the electrically insulative jackets.

17. The medical probe according to claim 16, wherein a distal portion of each of the plurality of electrically insulative jackets tapers outward and inward, following a curvature of the outer portion of the sinusoidal-like member.

18. The medical probe according to claim 16, a distal portion of each of the plurality of electrically insulative jackets abuts the distal portion of an adjacent insulative jacket.

19. The medical probe according to claim 15, further comprising:

two electrodes coupled to a respective spine for each spine of the plurality of spines, the plurality of spines comprising a first spine and a second spine, the first spine having a single cross-section extending from a proximal portion of the first spine to approximately a midpoint of the first spine and thereafter dividing into at least two discrete cross sections to the distal spine portion of the first spine, and the second spine having at least two discrete cross sections extending from a proximal portion of the second spine to approximately a midpoint of the second spine and thereafter combining into a single cross section extending to the distal spine portion of the second spine.

20. The medical probe according to claim 11, wherein the first radius measures between 31% and 35% of the height, wherein the second radius measures between 37% and 41% of the height, wherein the third radius measures between 31% and 35% of the height, and wherein a minimum width of the sinusoidal-like member measures between 23% and 27% of the height.

* * * * *